(12) United States Patent
Hagihara et al.

(10) Patent No.: US 10,479,974 B2
(45) Date of Patent: *Nov. 19, 2019

(54) METHOD, DEVICE AND KIT FOR MASS CULTIVATION OF CELLS USING POLYIMIDE POROUS MEMBRANE

(71) Applicant: UBE INDUSTRIES, LTD., Ube-shi, Yamaguchi (JP)

(72) Inventors: Masahiko Hagihara, Ube (JP); Motohisa Shimizu, Ube (JP); Yukinori Wada, Ube (JP)

(73) Assignee: UBE INDUSTRIES, LTD., Yamaguchi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/545,609

(22) PCT Filed: Jan. 26, 2016

(86) PCT No.: PCT/JP2016/052217
§ 371 (c)(1),
(2) Date: Jan. 11, 2018

(87) PCT Pub. No.: WO2016/121773
PCT Pub. Date: Aug. 4, 2016

(65) Prior Publication Data
US 2018/0016547 A1 Jan. 18, 2018

(30) Foreign Application Priority Data

Jan. 26, 2015 (JP) ................................ 2015-012470
Jan. 26, 2015 (JP) ................................ 2015-012544

(51) Int. Cl.
| | | |
|---|---|---|
| *C12N 5/00* | (2006.01) | |
| *C12N 1/14* | (2006.01) | |
| *C12N 1/16* | (2006.01) | |
| *C12N 1/20* | (2006.01) | |
| *C12N 5/04* | (2006.01) | |
| *C12M 1/00* | (2006.01) | |
| *C12M 1/12* | (2006.01) | |
| *C07K 14/535* | (2006.01) | |
| *C12M 3/06* | (2006.01) | |
| *C12N 5/077* | (2010.01) | |
| *C12N 5/071* | (2010.01) | |
| *C12P 21/02* | (2006.01) | |
| *A01N 1/02* | (2006.01) | |

(52) U.S. Cl.
CPC ......... *C12N 5/0068* (2013.01); *A01N 1/0231* (2013.01); *C07K 14/535* (2013.01); *C12M 23/20* (2013.01); *C12M 25/02* (2013.01); *C12M 27/16* (2013.01); *C12M 29/00* (2013.01); *C12N 1/14* (2013.01); *C12N 1/16* (2013.01); *C12N 1/20* (2013.01); *C12N 5/04* (2013.01); *C12N 5/0656* (2013.01); *C12N 5/0682* (2013.01); *C12P 21/02* (2013.01); *C12N 2533/30* (2013.01); *C12N 2535/00* (2013.01)

(58) Field of Classification Search
CPC ... C12N 1/14; C12N 1/20; C12N 5/04; C12N 5/0682; C12N 5/0656; C12N 5/0068; C12N 1/16; C12N 2535/00; C12N 2533/30; A01N 1/0231; C12P 21/02; C07K 14/535; C12M 29/00; C12M 27/16; C12M 23/20; C12M 25/02
See application file for complete search history.

(56) References Cited

U.S. PATENT DOCUMENTS

| | | | | |
|---|---|---|---|---|
| 4,228,243 | A * | 10/1980 | Iizuka | ................ C12M 23/34 435/294.1 |
| 5,071,760 | A | 12/1991 | Watanabe et al. | |
| 6,214,574 | B1 * | 4/2001 | Kopf | ................ B01D 61/32 435/170 |
| 2010/0041146 | A1 | 2/2010 | Kambayashi et al. | |
| 2011/0290112 | A1 * | 12/2011 | Liu | ................ B01D 53/228 95/54 |
| 2011/0318556 | A1 * | 12/2011 | Ohya | ................ C08J 9/28 428/216 |
| 2012/0207999 | A1 * | 8/2012 | Ohya | ................ C08J 5/18 428/220 |
| 2012/0308531 | A1 | 12/2012 | Pinxteren et al. | |
| 2018/0163174 | A1 | 6/2018 | Hagihara et al. | |

FOREIGN PATENT DOCUMENTS

| | | | |
|---|---|---|---|
| EP | 3 026 108 | A1 | 6/2016 |
| JP | 62-065681 | A | 3/1987 |
| JP | 63-196286 | A | 8/1988 |
| JP | 63-198975 | A | 8/1988 |
| JP | 63-198978 | A | 8/1988 |
| JP | 63196286 | * | 8/1988 |

(Continued)

OTHER PUBLICATIONS

H. Ahern. Hollow Fiber Bioreactor Systems Increase Cell Culture Yield. The Scientist Magazine, Feb. 1990, 2 pages. (Year: 1990).*
Inloes et al. Hollow-Fiber Membrane Bioreactors Using Immobilized *E. coli* for Protein Synthesis. Biotechnology and Bioengineering (1983), v25, p. 2653-2681. (Year: 1983).*
Maenosono, Hirotaka et al., "A Transparent Polyimide Film as a Biological Cell Culture Sheet with Microstructures," *Journal of Biomaterials and Nanobiotechnology* (2014; accepted Dec. 28, 2013); 5:17-23.
International Search Report dated May 10, 2016 corresponding to International Patent Application No. PCT/JP/2016/052217, filed on Jan. 26, 2016; 2 pages.

(Continued)

*Primary Examiner* — Sean C. Barron
(74) *Attorney, Agent, or Firm* — Mintz Levin Cohn Ferris Glovsky and Popeo PC

(57) ABSTRACT

The present invention pertains to a method for the mass cultivation of cells, and a cell cultivation device and kit. The present invention further pertains to a continuous cell cultivation method and a continuous cell cultivation device in which a carrier is used.

16 Claims, 9 Drawing Sheets

(56) References Cited

FOREIGN PATENT DOCUMENTS

| JP | H0630570 | B2 |   | 4/1994 |   |
|----|----------|----|---|--------|---|
| JP | H078229 | B2 |   | 2/1995 |   |
| JP | 07-313151 | A |   | 12/1995 |   |
| JP | 2001-190270 | A |   | 7/2001 |   |
| JP | 2004-344002 | A |   | 12/2004 |   |
| JP | 4510425 | B2 |   | 7/2010 |   |
| JP | 2011-219585 | A |   | 11/2011 |   |
| JP | 2011-219586 | A |   | 11/2011 |   |
| WO | 03/054174 | A1 |   | 7/2003 |   |
| WO | 2008/084857 | A1 |   | 7/2008 |   |
| WO | 2010/038873 | A1 |   | 4/2010 |   |
| WO | WO-2011125988 | A1 | * | 10/2011 | ......... B01D 67/0006 |
| WO | 2015/012415 | A1 |   | 1/2015 |   |

OTHER PUBLICATIONS

Julien, Sylvie et al., "Implantation of ultrathin, biofunctionalized polyimide membranes into the subretinal space of rats," *Bomaterials* (Mar. 8, 2011 online); 32:3890-3898.

Kawakami, Hiroyoshi, "Cell Culture on Nano- or Micro-relief pattern Surface," *Membrane* (Jul. 10, 2007); 32(5):266-270 (see, English Abstract).

Kim, Sang-Bok et al., "Use of a poly(ether imide) coating to improve corrosion resistance and biocompatibility of magnesium (Mg) implant for orthopedic applications," *Journal of Biomedical Materials Research A* (Jun. 2013; published online Nov. 27, 2012); 101A(6):1708-1715.

Maenosono, Hirotaka et al., "Cultivation of OP9 Cells onto Organic Flexible Sheets with Transferred Micropatterns," *IEICE Technical Report* (Apr. 2013) 113(18):37-42 (see, English Abstract).

Tao, Chun-Te et al., "Polyetherimide membrane formation by the cononsolvent system and its biocompatibility of MG63 cell line," *Journal of Membrane Science* (2006; accepted Jun. 10, 2005); 269:6674.

Abeille, F. et al., "Continuous microcarrier-based cell culture in a benchtop microfluidic bioreactor," *Lab Chip* (accepted Jun. 26, 2014); 14:3510-3518.

Ogata, Masaaki et al., "Continuous Culture of CHO-K1 Cells Producing Thrombomodulin and Estimation of Culture Conditions," *Journal of Fermentation and Bioengineering* (1994; accepted Sep. 6, 1993); 77(1):46-51.

Otsuji, Tomomi G. et al., "A 3D Sphere Culture System Containing Functional Polymers for Large-Scale Human Pluripotent Stem Cell Production," *Stem Cell Reports* (May 6, 2014); 2:734-745.

\* cited by examiner

METHOD, DEVICE AND KIT FOR MASS CULTIVATION OF CELLS USING POLYIMIDE POROUS MEMBRANE

TECHNICAL FIELD

The present invention relates to a method for mass culturing of cells, and to a cell culturing apparatus and kit.

BACKGROUND ART

Cell Culturing

Cells generally exist as three-dimensional aggregates in the body. However, when cells are cultured in an artificial environment, it is common to use the classical plate culture method in which the cells are cultured two-dimensionally in a manner plated as a monolayer on the bottom of the culturing vessel, or a suspension culture method in which cells are cultured while dispersed in a liquid culture solution. Cells most suited for the plate culture method are cells having relatively high adhesion, but even when such suitable cells are used, differences in the culturing environment can often result in significant changes in the properties of the cells. With suspension culture methods as well, certain cells are suitable while others are not.

With increasing demand for in vivo proteins to be used for medical purposes, such as vaccines, enzymes, hormones, antibodies, cytokines and the like, interest is becoming increasingly focused on mass production of such in vivo proteins by cell culturing. In addition, with ever increasing interest in cell transplantation for regenerative medicine, greater focus is being directed toward methodologies for efficient and convenient culturing of large volumes of cells.

For suspended cells of E. coli and the like, research is being conducted on techniques for mass culturing in large-scale culturing tanks. Mass culturing of suspended cells using large-scale culturing tanks requires large volumes of culture solution and an agitating apparatus. Increasing focus is also being directed toward research in which substances are produced using adherent cells, as research on such cells continues to progress. When it is attempted to perform mass culturing of adherent cells, the cells will only expand two-dimensionally when the classical plate culture method is employed, and therefore a large culturing area is necessary.

A method using a bioreactor or cell culture support has been reported as a method of culturing large volumes of cells in a three-dimensional environment (NPL 1 and PTL 1). Methods using a bioreactor include a method in which a fibrous material such as a glass fiber material is accumulated in a column, and the cells are continuously cultured in the space to produce a substance (PTL 2). Microcarriers, which are microparticles on which cells can adhere and grow, are being widely studied as typical cell culturing supports (PTLs 3 and 4).

PTL 4 mentions viral production as an example, and teaches that, in cell culturing methods using microcarriers, the most important factor for raising production volume and increasing efficiency is to reach a high-density cell culture. Also important is whether the cells can efficiently and conveniently proliferate, and can be transplanted and seeded onto the microcarrier support. In this regard, in a cell culturing system using microcarriers it is necessary to carry out sufficient agitation and diffusion so that the microcarriers do not aggregate together. Since this requires a volume space allowing adequate agitation and diffusion of the culture solution in which the microcarriers are dispersed, there is a limit to the density at which the cells can be cultured. In addition, issues still remain in terms of volume and efficiency because it is necessary to separate the fine particles with a separable filter in order to separate the microcarriers and the culture solution.

Methods of continuous mass culturing of spheroid cells by three-dimensional culturing using methyl cellulose or gellan gum have also been devised as different methods from microcarrier culturing (NPLs 2 and 3), but such methods are not only limited to use with spheroid cells, but they also require complex procedures such as precise monitoring of the state of culturing to obtain fine granular spheroid clumps.

A desire exists to develop and establish a cell culturing method that can culture large numbers of cells by a process that is convenient and automatable.

Bioreactors and microcarrier culturing methods using hollow fiber cultures or cellulose cubes have been widely developed as systems for culturing of adherent cells using a support. The classical methodology, as described in PTL 5, involves continuously feeding a medium that has been aerated with air containing 5% $CO_2$, to aggregates of the cells and a culturing support, to allow continuous culturing to be carried out. Such methods have been difficult, however, because the apparatuses used are complex. At actual field of production, microcarriers are most commonly used as cell culture supports (for example, NPL 4). Methods of prolonged culturing using such microcarriers in combination with a medium supply system also continue to be studied (PTLs 6 and 7, and NPL 5). Even in methods using microcarriers, however, the apparatuses used are often complicated and can present a problem in that the culturing efficiency cannot be adequately improved over biological systems, for example. PTL 8 describes a methodological idea thought to be more efficient, but it does not describe a specific example of actual culturing, and specific materials suited for the methodology are not mentioned. Hence, there is a demand for establishment of a more convenient and efficient continuous cell culturing apparatus.

Porous Polyimide Film

The term "polyimide" is a general term for polymers including imide bonds in the repeating unit. An "aromatic polyimide" is a polymer in which aromatic compounds are directly linked by imide bonds. An aromatic polyimide has an aromatic-aromatic conjugated structure via an imide bond, and therefore has a strong rigid molecular structure, and since the imide bonds provide powerful intermolecular force, it has very high levels of thermal, mechanical and chemical properties.

Porous polyimide films have been utilized in the prior art for filters and low permittivity films, and especially for battery-related purposes, such as fuel cell electrolyte membranes and the like. PTLs 9 to 11 describe porous polyimide films with numerous macro-voids, having excellent permeability for gases and the like, high porosity, excellent smoothness on both surfaces, relatively high strength and, despite high porosity, also excellent resistance against compression stress in the film thickness direction. All of these are porous polyimide films formed via amic acid.

CITATION LIST

Patent Literature

[PTL 1] Japanese Patent Application SHO No. 60-205822
[PTL 2] WO2008/084857
[PTL 3] Japanese Unexamined Patent Publication HEI No. 7-313151

[PTL 4] WO2003/054174
[PTL 5] Japanese Examined Patent Publication HEI No. 6-30570
[PTL 6] Japanese Examined Patent Publication HEI No. 7-8229
[PTL 7] Japanese Patent No. 4510425
[PTL 8] Japanese Unexamined Patent Publication No. 2001-190270
[PTL 9] WO2010/038873
[PTL 10] Japanese Unexamined Patent Publication No. 2011-219585
[PTL 11] Japanese Unexamined Patent Publication No. 2011-219586

Non-Patent Literature

[NPL 1] Ogata et al., Journal of Fermentation and Bioengineering Vol. 77, No. 1, p. 46-51 1994
[NPL 2] Otsuji et al., Stem Cell Reports Vol. 2 734-745 May 6, 2014
[NPL 3] http://www.nissanchem.co.jp/news_relese/news/n2014_04_25.pdf
[NPL 4] GE Healthcare Life Sciences Application note 29-0929-38 AA
[NPL 5] F. Abeille et al., Lab Chip, 2014, 14, 3510

DISCLOSURE OF THE INVENTION

Problems to be Solved by the Invention

It is an object of the present invention to provide a method for mass culturing of cells, and to a cell culturing apparatus and kit. It is another object of the invention to provide a more convenient and efficient continuous cell culturing apparatus and continuous cell culturing method.

Means for Solving the Problems

The present invention preferably includes, but is not limited to, the following modes.
[Mode 1]
A mass cell culturing method including:
(1) applying cells to a porous polyimide film, and
(2) applying the porous polyimide film to which the cells have been applied, to a cell culture medium and performing culturing.
[Mode 2]
The method according to mode 1, using two or more porous polyimide films layered either above and below or left and right in the cell culture medium.
[Mode 3]
The method according to mode 1 or 2, wherein the porous polyimide films are:
  i) folded,
  ii) wound into a roll,
  iii) connected as sheets or fragments by a filamentous structure, or
  iv) bound into a rope, to be suspended or fixed in the cell culture medium in the cell culturing vessel.
[Mode 4]
The method according to any one of modes 1 to 3, wherein in the culturing of step (2), all or some of the porous polyimide films are not in contact with the liquid phase of the cell culture medium.
[Mode 5]
The method according to any one of modes 1 to 4, wherein in the culturing of step (2), the total volume of the cell culture medium in the cell culturing vessel is 10,000 times or less of the total sum of the porous polyimide film volume including the cell survival zone.
[Mode 6]
The method according to any one of modes 1 to 5, wherein in the culturing of step (2), the total volume of the cell culture medium in the cell culturing vessel is 100 times or less of the total sum of the porous polyimide film volume including the cell survival zone.
[Mode 7]
The method according to any one of modes 1 to 6, wherein the culturing in step (2) is carried out in a system in which a cell culture medium is continuously or intermittently supplied to a cell culturing vessel from cell culture medium supply means installed outside of the cell culturing vessel.
[Mode 8]
The method according to mode 7, wherein the cell culture medium is circulated between the cell culture medium supply means and the cell culturing vessel.
[Mode 9]
The method according to mode 7 or 8, wherein the system is a cell culturing apparatus including a culturing unit which is the cell culturing vessel, and a culture medium-supply unit which is the cell culture medium supply means, wherein
the culturing unit is a culturing unit that houses one or more porous polyimide films to support cells, and that comprises a culture medium supply port and a culture medium discharge port, and
the culture medium-supply unit is a culture medium-supply unit comprising a culture medium housing vessel, a culture medium supply line, and a liquid conveyance pump that conveys the medium continuously or intermittently through the culture medium supply line, the first end of the culture medium supply line contacting the medium in the culture medium housing vessel, and the second end of the culture medium supply line being in communication with the culturing unit interior via the culture medium supply port of the culturing unit.
[Mode 10]
The method according to mode 9, wherein the culturing unit is a culturing unit that does not comprise an air supply port and air discharge port.
[Mode 11]
The method according to mode 9 or 10, wherein the culturing unit further comprises a culture medium discharge line, the first end of the culture medium discharge line being connected to the culture medium housing vessel, the second end of the culture medium discharge line being in communication with the culturing unit interior via the culture medium discharge port of the culturing unit, and the medium being able to circulate through the culture medium-supply unit and the culturing unit.
[Mode 12]
The method according to any one of modes 1 to 11, wherein the cells are selected from the group consisting of animal cells, insect cells, plant cells, yeast cells and bacteria.
[Mode 13]
The method according to mode 12, wherein the animal cells are cells derived from an animal belonging to the subphylum Vertebrata.
[Mode 14]
The method according to mode 12, wherein the bacteria are selected from the group consisting of lactic acid bacteria, *E. coli, Bacillus subtilis* and cyanobacteria.

[Mode 15]
The method according to any one of modes 1 to 14, wherein the porous polyimide film is a porous polyimide film including a polyimide obtained from a tetracarboxylic dianhydride and a diamine.

[Mode 16]
The method according to mode 15, wherein the porous polyimide film is a colored porous polyimide film obtained by forming a polyamic acid solution composition including a polyamic acid solution obtained from a tetracarboxylic dianhydride and a diamine, and a coloring precursor, and then heat treating it at 250° C. or higher.

[Mode 17]
The method according to mode 15 or 16, wherein the porous polyimide film is a porous polyimide film with a multilayer structure, having two different surface layers and a macro-void layer.

[Mode 18]
A cell culturing apparatus for use in the method according to any one of modes 1 to 17, including a porous polyimide film.

[Mode 19]
A cell culturing apparatus according to mode 18, wherein two or more porous polyimide films are layered either above and below or left and right.

[Mode 20]
A kit for use in the method according to any one of modes 1 to 17, including a porous polyimide film.

[Mode 21]
The use of a porous polyimide film for the method according to any one of modes 1 to 17.

[Mode 22]
A cell culturing apparatus, including:
a culturing unit that houses one or more porous polyimide films to support cells, and that comprises a culture medium supply port and a culture medium discharge port, and
a culture medium-supply unit comprising a culture medium housing vessel, a culture medium supply line, and a liquid conveyance pump that conveys the medium continuously or intermittently through the culture medium supply line, the first end of the culture medium supply line contacting the medium in the culture medium housing vessel, and the second end of the culture medium supply line being in communication with the culturing unit interior via the culture medium supply port of the culturing unit.

[Mode 23]
A cell culturing apparatus according to mode 22, wherein the culturing unit does not comprise an air supply port, an air discharge port and an oxygen exchange membrane.

[Mode 24]
A cell culturing apparatus according to mode 22, wherein the culturing unit further comprises an air supply port and an air discharge port, or an oxygen exchange membrane.

[Mode 25]
A cell culturing apparatus according to mode 24, wherein the air supply port and the air discharge port are, respectively, a 5% $CO_2$ gas-containing air supply port and a 5% $CO_2$ gas-containing air discharge port.

[Mode 26]
A cell culturing apparatus according to any one of modes 22 to 25, wherein the culturing unit does not have means for agitating the porous polyimide film.

[Mode 27]
A cell culturing apparatus according to any one of modes 22 to 25, wherein the culturing unit further has means for agitating the porous polyimide film.

[Mode 28]
A cell culturing apparatus according to any one of modes 22 to 27, wherein the culturing unit further comprises a culture medium discharge line, the first end of the culture medium discharge line being connected to the culture medium housing vessel, the second end of the culture medium discharge line being in communication with the culturing unit interior via the culture medium discharge port of the culturing unit, and the medium being able to circulate through the culture medium-supply unit and the culturing unit.

[Mode 29]
A cell culturing apparatus according to any one of modes 22 to 27, wherein the culturing unit further comprises a culture medium discharge line, the first end of the culture medium discharge line being connected to a culture medium collecting unit and the second end of the culture medium discharge line being in communication with the culturing unit interior via the culture medium discharge port of the culturing unit, and the discharged medium can be collected in the culture medium collecting unit.

[Mode 30]
A cell culturing apparatus according to any one of modes 22 to 29, further including means for shaking the culturing unit.

[Mode 31]
A cell culturing apparatus according to any one of modes 22 to 30, wherein the culturing unit comprises a flexible bag.

[Mode 32]
A cell culturing apparatus according to mode 31, wherein the flexible bag is a gas-permeable plastic bag.

[Mode 33]
A cell culturing apparatus according to any one of modes 22 to 32, wherein the one or more porous polyimide films are mounted on a rigid body inclined at an angle of no greater than 45° with respect to the horizontal, the second end of the culture medium supply line is installed so that the medium is supplied from a region near the top end of the porous polyimide films, and the second end of the culture medium discharge line is installed so that the medium is discharged from a region near the bottom end of the porous polyimide films.

[Mode 34]
A cell culturing apparatus according to mode 33, wherein the rigid body is a metal mesh.

[Mode 35]
A cell culturing apparatus according to mode 33 or 34, wherein the one or more porous polyimide films and the rigid body are housed in a housing, the housing being in turn housed in the culturing unit interior.

[Mode 36]
A cell culturing apparatus according to any one of modes 33 to 35, wherein a porous sheet having a larger mean pore size than that of the porous polyimide films is further mounted so as to cover all or a portion of the top surface of the one or more porous polyimide films.

[Mode 37]
A cell culturing apparatus according to mode 36, wherein the porous sheet is selected from the group consisting of nonwoven fabrics, gauze and sponges.

[Mode 38]
A cell culturing apparatus according to any one of modes 33 to 37, wherein a defoaming unit is further installed near the second end of the culture medium supply line.

[Mode 39]
A cell culturing apparatus according to any one of modes 22 to 38, wherein two or more porous polyimide films are layered above and below.

[Mode 40]

A cell culturing apparatus according to any one of modes 22 to 39, wherein the one or more porous polyimide films are folded.

[Mode 41]

A cell culturing apparatus according to any one of modes 22 to 40, wherein all or a portion of the one or more porous polyimide films is wetted with the medium.

[Mode 42]

A cell culturing apparatus according to any one of modes 22 to 41, wherein all or a portion of the surface of the one or more porous polyimide films is not in contact with the liquid phase of the medium.

[Mode 43]

A cell culturing apparatus according to any one of modes 22 to 42, wherein the volume of the medium in the culturing unit interior is 10,000 times or less of the total sum of the porous polyimide film volume including the cell survival zone.

[Mode 44]

A cell culturing apparatus according to any one of modes 22 to 43, wherein the volume of the medium in the culturing unit interior is 100 times or less of the total sum of the porous polyimide film volume including the cell survival zone.

[Mode 45]

A cell culturing apparatus according to any one of modes 22 to 43, wherein the volume of the medium in the culturing unit interior is 5 times or less of the total sum of the porous polyimide film volume including the cell survival zone.

[Mode 46]

A cell culturing apparatus according to any one of modes 22 to 45, wherein the porous polyimide film is a porous polyimide film including a polyimide obtained from a tetracarboxylic dianhydride and a diamine.

[Mode 47]

A cell culturing apparatus according to mode 46, wherein the porous polyimide film is a colored porous polyimide film obtained by forming a polyamic acid solution composition including a polyamic acid solution obtained from a tetracarboxylic dianhydride and a diamine, and a coloring precursor, and then heat treating it at 250° C. or higher.

[Mode 48]

A cell culturing method, including installing a cell culturing apparatus according to any one of modes 22 to 47 in an incubator and culturing cells.

[Mode 49]

A method for collection of a substance produced by cells, the method including:

installing a cell culturing apparatus according to any one of modes 22 to 47 in an incubator and culturing cells, and continuously or intermittently collecting the medium that has contacted with the cells.

[Mode 50]

The use of a porous polyimide film for a cell culturing apparatus according to any one of modes 22 to 47.

[Mode 51]

The use of a cell culturing apparatus according to any one of modes 22 to 47 for collection of a substance produced by cells.

Effect of the Invention

The present invention has been devised based on the knowledge that when a porous polyimide film is used for cell culturing, a large volume of cells can be efficiently cultured by placing multiple sheets together in a limited space in various forms. By the method of the invention it has become possible to culture large volumes of cells in an efficient and convenient manner in a small space.

In addition, by using a porous polyimide film as a cell culture support, the present invention allows cell culturing to be carried out conveniently, efficiently and continuously, even under conditions with a small culturing space and low medium volume.

Since a porous polyimide film has a low hydrophilic porous property, liquid is stably held in the porous polyimide film, and a wet environment is maintained that is resistant to drying. It is therefore possible to achieve survival and proliferation of cells even in very small amounts of medium, even when compared with conventional cell culturing apparatuses.

Furthermore, since it is possible to carry out culturing even if all or some of the porous polyimide film has been exposed to air, oxygen can be efficiently supplied to the cells, and mass culturing of cells is made possible.

According to the invention, the amount of medium used is extremely minimal, and the porous polyimide film used as the culture support can be exposed to a gas phase, thereby allowing oxygen supply to the cells to be adequately accomplished by diffusion. According to the invention, therefore, there is no particular need for an oxygen supply apparatus.

Moreover, because the porous polyimide film can be used in layers with increased adhesiveness, it is possible to stably carry out mass culturing of cells in an exceedingly small volume.

Furthermore, according to the invention, the medium is continuously or intermittently supplied adjacent to the porous polyimide film, thereby allowing cells to be continuously cultured without stagnation of the medium.

In addition, even when cells have reached confluency which is necessary for subculturing of conventional adherent cells, according to the invention a porous polyimide film having a space in which the cells are not seeded and/or where the cells can adhere may be attached (for example, by clamping or layering) onto a cell culture support that has become confluent or subconfluent, to allow expanded culturing without using trypsin or the like that is used in the prior art.

MODE FOR CARRYING OUT THE INVENTION

I. Cell Culturing Method

Figure 1:
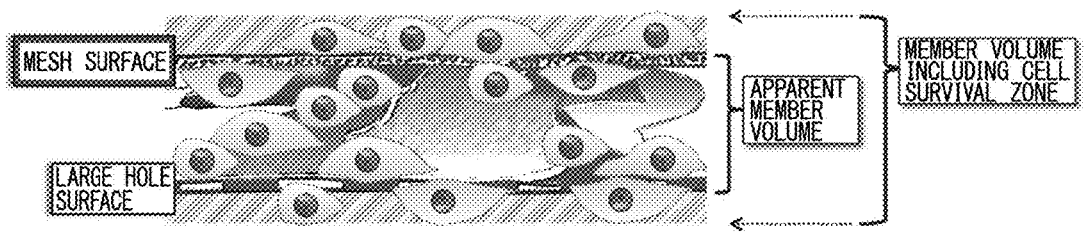
FIG. 1 is a model diagram of cell culturing using a porous polyimide film.

The present invention relates to a mass cell culturing method. The entire content of International Application Number PCT/JP2014/070407 is incorporated herein by reference.

The cell culturing method of the invention includes applying cells to a porous polyimide film and culturing them. The present inventors have found that a porous polyimide film is suitable for adhesion and culturing of cells, and have thereupon completed this invention. The method of the invention includes applying cells to a porous polyimide film and culturing the cells on the surface or in the interior of the polyimide film.

1. Application of Cells to Porous Polyimide Film

There are no particular restrictions on the specific steps for application of the cells to the porous polyimide film. It is possible to carry out the steps described throughout the present specification, or to employ any desired method suited for applying cells to a film-like support. Application of cells to the porous polyimide film in the method of the invention includes, but is not limited to, the following modes.

(A) A mode including a step of seeding cells on the surface of a porous polyimide film;

(B) A mode including a step of:

placing a cell suspension on the dried surface of a porous polyimide film, allowing it to stand, or moving the porous polyimide film to promote efflux of the liquid, or stimulating part of the surface to cause absorption of the cell suspension into the film, and retaining the cells in the cell suspension inside the film and allowing the water to flow out; and (C) A mode including a step of:

wetting one or both sides of a porous polyimide film with a cell culture solution or a sterilized liquid, loading a cell suspension into the wetted porous polyimide film, and retaining the cells in the cell suspension inside the film and allowing the water to flow out.

Mode (A) includes a step of directly seeding cells or a cell mass on the surface of a porous polyimide film. Alternatively, it includes a mode of placing a porous polyimide film in a cell suspension and wetting the cell culture solution from the surface of the film.

Cells seeded on the surface of a porous polyimide film adhere to the porous polyimide film and infiltrate into the interiors of the pores. Preferably, the cells adhere spontaneously to the porous polyimide film without applying any particular exterior physical or chemical force. The cells that have been seeded on the surface of the porous polyimide film can stably grow and proliferate on the surface and/or in the interior of the film. The cells may be in a variety of different forms, depending on the location of the film used for growth and proliferation.

For mode (B), a cell suspension is placed on the dried surface of a porous polyimide film. The porous polyimide film is allowed to stand, or the porous polyimide film is moved to promote efflux of the liquid, or part of the surface is stimulated to cause absorption of the cell suspension into the film, so that the cell suspension permeates into the film. While it is not our intention to be constrained by theory, this is believed to be due to the properties of each of the surface forms of the porous polyimide film. According to this mode, the cells are absorbed and seeded in the locations of the film where the cell suspension has been loaded.

Alternatively, as according to mode (C), after all or a portion of one or both sides of the porous polyimide film has been wetted with the cell culture solution or sterilized liquid, the cell suspension may be loaded into the wetted porous polyimide film. This will significantly increase the transit rate of the cell suspension.

For example, a method of wetting a portion of the film edges, for the main purpose of preventing fly loss of the film, may be used (hereunder referred to as "single-point wetting method"). The single-point wetting method is nearly the same as the dry method (mode (B)) in which the film essentially is not wetted. However, it is possible that cell solution permeation through the film is more rapid at the small wetted portions. There may also be used a method in which all of one or both sides of the porous polyimide film that have been thoroughly wetted (hereunder this will also be referred to as "wet film") is loaded with a cell suspension (this will hereunder be referred to as "wet film method"). In this case, the entire porous polyimide film has a greatly increased transit rate for the cell suspension.

According to modes (B) and (C), the cells in the cell suspension are retained in the film, while the water flows out. This allows treatment such as increasing the concentration of cells in the cell suspension and flowing out of unwanted non-cellular components together with the water.

Mode (A) will also be referred to as "natural seeding", and modes (B) and (C) as "suction seeding".

Preferably, but not restrictively, the viable cells are selectively retained in the porous polyimide film. Thus, according to a preferred mode of the invention, the viable cells are retained in the porous polyimide film, and the dead cells preferentially flow out together with the water.

The sterilized liquid used for mode (C) is not particularly restricted, and may be a sterilized buffering solution or sterilized water. A buffering solution may be, for example, (+) or (−) Dulbecco's PBS, or (+) or (−) Hank's Balanced Salt Solution. Examples of buffering solutions are listed in Table 1 below.

TABLE 1

| Component | Concentration (mmol/L) | Concentration (g/L) |
|---|---|---|
| NaCl | 137 | 8.00 |
| KCl | 2.7 | 0.20 |
| $Na_2HPO_4$ | 10 | 1.44 |
| $KH_2PO_4$ | 1.76 | 0.24 |
| pH (—) | 7.4 | 7.4 |

In the method of the invention, application of cells to the porous polyimide film further includes a mode of adding adherent cells in a floating state as a suspension together with the porous polyimide film, to adhere the cells with the film (entangling). For example, for application of the cells to the porous polyimide film in the cell culturing method of the invention, the cell culture medium, the cells and one or more of the porous polyimide films may be placed in the cell culturing vessel. When the cell culture medium is a liquid, the porous polyimide film is in a floating state in the cell culture medium. The cells can adhere to the porous polyimide film due to the properties of the porous polyimide film. Thus, even with cells that are not suited for natural suspension culture, the porous polyimide film allows culturing in a floating state in the cell culture medium. The cells also preferably spontaneously adhere to the porous polyimide film. Here, "adhere spontaneously" means that the cells are retained on the surface or in the interior of the porous polyimide film without applying any particular exterior physical or chemical force.

Cell culturing can be classified into culturing where the cultured cells are adhesion culture-type cells or suspension culture-type cells, depending on the state in the cell culture. Adhesion culture-type cells are cultured cells that adhere and grow on a culturing vessel, with the medium being exchanged at the time of subculture. Suspension culture-type cells are cultured cells that grow in a suspended state in a medium, and generally the medium is not exchanged with each subculture but dilution culture is carried out. Because suspension culture allows culturing in a suspended state, i.e. in a liquid, mass culturing becomes possible, and because it is three-dimensional culturing, unlike with adherent cells that grow only on the culturing vessel surface, the advantage of increased culturable cell count per unit space is afforded.

In the mass culturing method of the invention, when the porous polyimide film is used in a state suspended in the cell culture medium, two or more fragments of the porous polyimide film may be used. Since the porous polyimide film is a three-dimensional, flexible thin-film, using such fragments that are suspended in the culture solution, for example, allows a porous polyimide film with a large culturable surface area to be added into a fixed volume of cell culture medium. In the case of normal culturing, the container base area constitutes the area limit in which cell culture can be accomplished, but with cell culturing using the porous polyimide film of the invention, all of the large surface area of the previously added porous polyimide film constitutes area in which cell culturing can be accomplished. The porous polyimide film allows the cell culture solution to pass through, allowing supply of nutrients, oxygen and the like even into the folded film, for example. In addition, since the porous polyimide film is completely different from a conventional plate culture in that it is a cell culturing substrate having a three-dimensional and flexible structure, it allows culturing of cells with an adhering property in culturing vessels of various shapes, materials and sizes (for example, dishes, flasks, tanks or bags), regardless of the shape of the culturing vessel.

The sizes and shapes of the porous polyimide film fragments are not particularly restricted. The shapes may be as desired, such as circular, elliptical, quadrilateral, triangular, polygonal or string-like.

Because the porous polyimide film of the invention is flexible, it can be used with varying shapes. Instead of a flat form, the porous polyimide film can also be used by working into a three-dimensional shape. For example, porous polyimide films may be: i) folded, ii) wound into a roll, iii) connected as sheets or fragments by a filamentous structure, or iv) bound into a rope, for suspension or fixing in the cell culture medium in the cell culturing vessel. By forming into shapes such as i) to iv), it is possible to place a large amount of porous polyimide films into a fixed volume of cell culture medium, similar to using fragments. Furthermore, since each fragment can be treated as an aggregate, it is possible to aggregate and move the cell masses together, for overall high applicability.

With the same concept as fragment aggregates, two or more porous polyimide films may be used in a layered form either above and below or left and right in the cell culture medium. Layering includes a mode in which portions of the porous polyimide films overlap. Layered culturing allows culturing of cells at high density in a narrow space. It is also possible to further layer a film on a film on which cells are already growing, setting it to create a multilayer of different cell types. The number of layered porous polyimide films is not particularly restricted.

Two or even more forms of the cell culturing method of the invention described above may be used in combination. For example, using any of the methods of modes (A) to (C), first the cells may be applied to the porous polyimide film and then the cell-adhered porous polyimide film may be used for suspension culture. Alternatively, the step of application to the porous polyimide film may be a combination of two or more of the methods of any of modes (A) to (C).

In the method of the invention, preferably the cells grow and proliferate on the surface or in the interior of the porous polyimide film. By the method of the invention it is possible to carry out continuous growth of cells for 2 days or longer, more preferably 4 days or longer and even more preferably 6 days or longer. In Example 1 described in the present specification, growth of cells was observed for at least 23 days.

2. Cells

There are no particular restrictions on the type of cells that can be utilized for the method of the invention, and it may be used for growth of any type of cells.

For example, the cells may be selected from the group consisting of animal cells, insect cells, plant cells, yeast cells and bacteria. Animal cells are largely divided into cells from animals belonging to the subphylum Vertebrata, and cells from non-vertebrates (animals other than animals belonging to the subphylum Vertebrata). There are no particular restrictions on the source of the animal cells, for the purpose of the present specification. Preferably, they are cells from an animal belonging to the subphylum Vertebrata. The subphylum Vertebrata includes the superclass Agnatha and the superclass Gnathostomata, the superclass Gnathostomata including the class Mammalia, the class Aves, the class Amphibia and the class Reptilia. Preferably, they are cells from an animal belonging to the class Mammalia, generally known as mammals. Mammals are not particularly restricted but include, preferably, mice, rats, humans, monkeys, pigs, dogs, sheep and goats.

There are also no particular restrictions on sources of plant cells, for the purpose of the present specification. Suitable cells are from plants including bryophytes, pteridophytes and spermatophytes.

Plants from which spermatophyte cells are derived include both monocotyledons and dicotyledons. While not restrictive, monocotyledons include Orchidaceae plants, Poaceae plants (rice, corn, barley, wheat, sorghum and the like) and Cyperaceae plants. Dicotyledons include plants belonging to many subclasses including the subclass Chrysanthemum, the subclass Magnoliidae and the subclass Rosidae.

Algae may be considered cell-derived organisms. These include different groups, from the eubacteria Cyanobacteria (blue-green algae), to eukaryotic monocellular organisms (diatoms, yellow-green algae, dinoflagellates and the like) and multicellular marine algae (red algae, brown algae and green algae).

There are no particular limitations on the types of archaebacteria or bacteria for the purpose of the present specification. Archaebacteria are composed of groups comprising methanogenic bacteria, extreme halophilic bacteria, thermophilic acidophilic bacteria, hyperthermophilic bacteria and the like. Bacteria are selected from the group consisting of, for example, lactic acid bacteria, E. coli, Bacillus subtilis and cyanobacteria.

The types of animal cells or plant cells that may be used for the method of the invention are not particularly restricted, but are preferably selected from the group consisting of pluripotent stem cells, tissue stem cells, somatic cells and germ cells.

The term "pluripotent stem cells", for the purpose of the invention, is intended as a comprehensive term for stem cells having the ability to differentiate into cells of a variety of tissues (pluripotent differentiating power). While not restrictive, pluripotent stem cells include embryonic stem cells (ES cells), induced pluripotent stem cells (iPS cells), embryonic germ cells (EG cells) and germ stem cells (GS cells). They are preferably ES cells or iPS cells. Particularly preferred are iPS cells, which are free of ethical problems, for example. The pluripotent stem cells used may be any publicly known ones, and for example, the pluripotent stem cells described in International Patent Publication No. WO2009/123349 (PCT/JP2009/057041) may be used.

The term "tissue stem cells" refers to stem cells that are cell lines capable of differentiation but only to limited specific tissues, though having the ability to differentiate into a variety of cell types (pluripotent differentiating power). For example, hematopoietic stem cells in the bone marrow are the source of blood cells, while neural stem cells differentiate into neurons. Additional types include hepatic stem cells from which the liver is formed and skin stem cells that form skin tissue. Preferably, the tissue stem cells are selected from among mesenchymal stem cells, hepatic stem cells, pancreatic stem cells, neural stem cells, skin stem cells and hematopoietic stem cells.

The term "somatic cells" refers to cells other than germ cells, among the cells composing a multicellular organism. In sexual reproduction these are not passed on to the next generation. Preferably, the somatic cells are selected from among hepatocytes, pancreatic cells, muscle cells, bone cells, osteoblasts, osteoclasts, chondrocytes, adipocytes, skin cells, fibroblasts, pancreatic cells, renal cells and lung cells, or blood cells such as lymphocytes, erythrocytes, leukocytes, monocytes, macrophages or megakaryocytes.

The term "germ cells" refers to cells having the role of passing on genetic information to the succeeding generation in reproduction. These include, for example, gametes for sexual reproduction, i.e. the ova, egg cells, sperm, sperm cells, and spores for asexual reproduction.

The cells may also be selected from the group consisting of sarcoma cells, established cell lines and transformants. The term "sarcoma" refers to cancer occurring in non-epithelial cell-derived connective tissue cells, such as the bone, cartilage, fat, muscle or blood, and includes soft tissue sarcomas, malignant bone tumors and the like. Sarcoma cells are cells derived from sarcoma. The term "established cell line" refers to cultured cells that are maintained in vitro for long periods and reach a stabilized character and can be semi-permanently subcultured. Cell lines derived from various tissues of various species including humans exist, such as PC12 cells (from rat adrenal medulla), CHO cells (from Chinese hamster ovary), HEK293 cells (from human embryonic kidney), HL-60 cells from (human leukocytes) and HeLa cells (from human cervical cancer), Vero cells (from African green monkey kidney epithelial cells), MDCK cells (from canine renal tubular epithelial cells) and HepG2 cells (from human hepatic cancer). The term "transformants" refers to cells with an altered genetic nature by extracellularly introduced nucleic acid (DNA and the like). Suitable methods are known for transformation of animal cells, plant cells and bacteria.

3. Porous Polyimide Film

Polyimide is a general term for polymers containing imide bonds in the repeating unit, and usually it refers to an aromatic polyimide in which aromatic compounds are directly linked by imide bonds. An aromatic polyimide has an aromatic-aromatic conjugated structure via an imide bond, and therefore has a strong rigid molecular structure, and since imide bonds have powerful intermolecular force, it has very high levels of thermal, mechanical and chemical properties.

The porous polyimide film used for the invention is preferably a porous polyimide film including (as the main component) a polyimide obtained from a tetracarboxylic dianhydride and a diamine, and more preferably it is a porous polyimide film comprising a polyimide obtained from a tetracarboxylic dianhydride and a diamine. The phrase "including as the main component" means that it essentially contains no components other than the polyimide obtained from a tetracarboxylic dianhydride and a diamine, as constituent components of the porous polyimide film, or that it may contain them but they are additional components that do not affect the properties of the polyimide obtained from the tetracarboxylic dianhydride and diamine.

This also includes colored porous polyimide films obtained by forming a polyamic acid solution composition containing a polyamic acid solution obtained from a tetracarboxylic acid component and a diamine component, and a coloring precursor, and then heat treating it at 250° C. or higher.

Polyamic Acid

A polyamic acid is obtained by polymerization of a tetracarboxylic acid component and a diamine component. A polyamic acid is a polyimide precursor that can be cyclized to a polyimide by thermal imidization or chemical imidization.

The polyamic acid used may be any one that does not have an effect on the invention, even if a portion of the amic acid is imidized. Specifically, the polyamic acid may be partially thermally imidized or chemically imidized.

When the polyamic acid is to be thermally imidized, there may be added to the polyamic acid solution, if necessary, an imidization catalyst, an organic phosphorus-containing compound, or fine particles such as inorganic fine particles or organic fine particles. Also, when the polyamic acid is to be chemically imidized, there may be added to the polyamic acid solution, if necessary, a chemical imidization agent, a dehydrating agent, or fine particles such as inorganic fine particles or organic fine particles. Even if such components are added to the polyamic acid solution, they are preferably added under conditions that do not cause precipitation of the coloring precursor.

Coloring Precursor

For the purpose of the invention, a coloring precursor is a precursor that generates a colored substance by partial or total carbonization under heat treatment at 250° C. or higher.

Coloring precursors to be used for the invention are preferably uniformly dissolved or dispersed in a polyamic acid solution or polyimide solution and subjected to thermal decomposition by heat treatment at 250° C. or higher, preferably 260° C. or higher, even more preferably 280° C. or higher and more preferably 300° C. or higher, and preferably heat treatment in the presence of oxygen such as air, at 250° C., preferably 260° C. or higher, even more preferably 280° C. or higher and more preferably 300° C. or higher, for carbonization to produce a colored substance, more preferably producing a black colored substance, with carbon-based coloring precursors being most preferred.

The coloring precursor, when being heated, first appears as a carbonized compound, but compositionally it contains other elements in addition to carbon, and also includes layered structures, aromatic crosslinked structures and tetrahedron carbon-containing disordered structures.

Carbon-based coloring precursors are not particularly restricted, and for example, they include tar or pitch such as petroleum tar, petroleum pitch, coal tar and coal pitch, coke, polymers obtained from acrylonitrile-containing monomers, ferrocene compounds (ferrocene and ferrocene derivatives), and the like. Of these, polymers obtained from acrylonitrile-containing monomers and/or ferrocene compounds are preferred, with polyacrylonitrile being preferred as a polymer obtained from an acrylonitrile-containing monomer.

The tetracarboxylic dianhydride used may be any tetracarboxylic dianhydride, selected as appropriate according to the properties desired. Specific examples of tetracarboxylic dianhydrides include biphenyltetracarboxylic dianhydrides such as pyromellitic dianhydride, 3,3',4,4'-biphenyltetracarboxylic dianhydride (s-BPDA) and 2,3,3',4'-biphenyltetracarboxylic dianhydride (a-BPDA), oxydiphthalic dianhydride, diphenylsulfone-3,4,3',4'-tetracarboxylic dianhydride, bis(3,4-dicarboxyphenyl)sulfide dianhydride, 2,2-bis(3,4-dicarboxyphenyl)-1,1,1,3,3,3-hexafluoropropane dianhydride, 2,3,3',4'-benzophenonetetracarboxylic dianhydride, 3,3',4,4'-benzophenonetetracarboxylic dianhydride, bis(3,4-dicarboxyphenyl)methane dianhydride, 2,2-bis(3,4-dicarboxyphenyl)propane dianhydride, p-phenylenebis(trimellitic acid monoester acid anhydride), p-biphenylenebis(trimellitic acid monoester acid anhydride), m-terphenyl-3,4,3',4'-tetracarboxylic dianhydride, p-terphenyl-3,4,3',4'-tetracarboxylic dianhydride, 1,3-bis(3,4-dicarboxyphenoxy)benzene dianhydride, 1,4-bis(3,4-dicarboxyphenoxy)benzene dianhydride, 1,4-bis(3,4-dicarboxyphenoxy)biphenyl dianhydride, 2,2-bis[(3,4-dicarboxyphenoxy)phenyl]propane dianhydride, 2,3,6,7-naphthalenetetracarboxylic dianhydride, 1,4,5,8-naphthalenetetracarboxylic dianhydride, 4,4'-(2,2-hexafluoroisopropylidene)diphthalic dianhydride, and the like. Also preferably used is an aromatic tetracarboxylic acid such as 2,3,3',4'-diphenylsulfonetetracarboxylic acid. These may be used alone or in appropriate combinations of two or more.

Particularly preferred among these are at least one type of aromatic tetracarboxylic dianhydride selected from the group consisting of biphenyltetracarboxylic dianhydride and pyromellitic dianhydride. As a biphenyltetracarboxylic dianhydride there may be suitably used 3,3',4,4'-biphenyltetracarboxylic dianhydride.

Any desired diamine may be used as a diamine. Specific examples of diamines include the following.

1) Benzenediamines with one benzene nucleus, such as 1,4-diaminobenzene(paraphenylenediamine), 1,3-diaminobenzene, 2,4-diaminotoluene and 2,6-diaminotoluene;

2) diamines with two benzene nuclei, including diaminodiphenyl ethers such as 4,4'-diaminodiphenyl ether and 3,4'-diaminodiphenyl ether, and 4,4'-diaminodiphenylmethane, 3,3'-dimethyl-4,4'-diaminobiphenyl, 2,2'-dimethyl-4,4'-diaminobiphenyl, 2,2'-bis(trifluoromethyl)-4,4'-diaminobiphenyl, 3,3'-dimethyl-4,4'-diaminodiphenylmethane, 3,3'-dicarboxy-4,4'-diaminodiphenylmethane, 3,3',5,5'-tetramethyl-4,4'-diaminodiphenylmethane, bis(4-aminophenyl)sulfide, 4,4'-diaminobenzanilide, 3,3'-dichlorobenzidine, 3,3'-dimethylbenzidine, 2,2'-dimethylbenzidine, 3,3'-dimethoxybenzidine, 2,2'-dimethoxybenzidine, 3,3'-diaminodiphenyl ether, 3,4'-diaminodiphenyl ether, 4,4'-diaminodiphenyl ether, 3,3'-diaminodiphenyl sulfide, 3,4'-diaminodiphenyl sulfide, 4,4'-diaminodiphenyl sulfide, 3,3'-diaminodiphenylsulfone, 3,4'-diaminodiphenylsulfone, 4,4'-diaminodiphenylsulfone, 3,3'-diaminobenzophenone, 3,3'-diamino-4,4'-dichlorobenzophenone, 3,3'-diamino-4,4'-dimethoxybenzophenone, 3,3'-diaminodiphenylmethane, 3,4'-diaminodiphenylmethane, 4,4'-diaminodiphenylmethane, 2,2-bis(3-aminophenyl)propane, 2,2-bis(4-aminophenyl)propane, 2,2-bis(3-aminophenyl)-1,1,1,3,3,3-hexafluoropropane, 2,2-bis(4-aminophenyl)-1,1,1,3,3,3-hexafluoropropane, 3,3'-diaminodiphenyl sulfoxide, 3,4'-diaminodiphenyl sulfoxide and 4,4'-diaminodiphenyl sulfoxide;

3) diamines with three benzene nuclei, including 1,3-bis(3-aminophenyl)benzene, 1,3-bis(4-aminophenyl)benzene, 1,4-bis(3-aminophenyl)benzene, 1,4-bis(4-aminophenyl)benzene, 1,3-bis(4-aminophenoxy)benzene, 1,4-bis(3-aminophenoxy)benzene, 1,4-bis(4-aminophenoxy)benzene, 1,3-bis(3-aminophenoxy)-4-trifluoromethylbenzene, 3,3'-diamino-4-(4-phenyl)phenoxybenzophenone, 3,3'-diamino-4,4'-di(4-phenylphenoxy) benzophenone, 1,3-bis(3-aminophenyl sulfide)benzene, 1,3-bis(4-aminophenyl sulfide)benzene, 1,4-bis(4-aminophenyl sulfide)benzene, 1,3-bis(3-aminophenylsulfone)benzene, 1,3-bis(4-aminophenylsulfone)benzene, 1,4-bis(4-aminophenylsulfone)benzene, 1,3-bis[2-(4-aminophenyl)isopropyl]benzene, 1,4-bis[2-(3-aminophenyl)isopropyl]benzene and 1,4-bis[2-(4-aminophenyl) isopropyl]benzene;

4) diamines with four benzene nuclei, including 3,3'-bis(3-aminophenoxy)biphenyl, 3,3'-bis(4-aminophenoxy)biphenyl, 4,4'-bis(3-aminophenoxy)biphenyl, 4,4'-bis(4-aminophenoxy)biphenyl, bis[3-(3-aminophenoxy)phenyl]ether, bis[3-(4-aminophenoxy)phenyl]ether, bis[4-(3-aminophenoxy)phenyl]ether, bis[4-(4-aminophenoxy)phenyl]ether, bis[3-(3-aminophenoxy)phenyl]ketone, bis[3-(4-aminophenoxy)phenyl]ketone, bis[4-(3-aminophenoxy)phenyl]ketone, bis[4-(4-aminophenoxy) phenyl]ketone, bis[3-(3-aminophenoxy)phenyl]sulfide, bis[3-(4-aminophenoxy)phenyl]sulfide, bis[4-(3-aminophenoxy)phenyl]sulfide, bis[4-(4-aminophenoxy) phenyl]sulfide, bis[3-(3-aminophenoxy)phenyl]sulfone, bis[3-(4-aminophenoxy)phenyl]sulfone, bis[4-(3-aminophenoxy)phenyl]sulfone, bis[4-(4-aminophenoxy)phenyl]sulfone, bis[3-(3-aminophenoxy)phenyl]methane, bis[3-(4-aminophenoxy)phenyl]methane, bis[4-(3-aminophenoxy)phenyl]methane, bis[4-(4-aminophenoxy)phenyl]methane, 2,2-bis[3-(3-aminophenoxy)phenyl]propane, 2,2-bis[3-(4-aminophenoxy)phenyl]propane, 2,2-bis[4-(3-aminophenoxy)phenyl]propane, 2,2-bis[4-(4-aminophenoxy)phenyl]propane, 2,2-bis[3-(3-aminophenoxy)phenyl]-1,1,1,3,3,3-hexafluoropropane, 2,2-bis[3-(4-aminophenoxy)phenyl]-1,1,1,3,3,3-hexafluoropropane, 2,2-bis[4-(3-aminophenoxy)phenyl]-1,1,1,3,3,3-hexafluoropropane and 2,2-bis[4-(4-aminophenoxy)phenyl]-1,1,1,3,3,3-hexafluoropropane.

These may be used alone or in mixtures of two or more. The diamine used may be appropriately selected according to the properties desired.

Preferred among these are aromatic diamine compounds, with 3,3'-diaminodiphenyl ether, 3,4'-diaminodiphenyl ether, 4,4'-diaminodiphenyl ether, paraphenylenediamine, 1,3-bis(3-aminophenyl)benzene, 1,3-bis(4-aminophenyl)benzene, 1,4-bis(3-aminophenyl)benzene, 1,4-bis(4-aminophenyl)benzene, 1,3-bis(4-aminophenoxy)benzene and 1,4-bis(3-aminophenoxy)benzene being preferred for use. Particularly preferred is at least one type of diamine selected from the group consisting of benzenediamines, diaminodiphenyl ethers and bis(aminophenoxy)phenyl.

From the viewpoint of heat resistance and dimensional stability under high temperature, the porous polyimide film is preferably formed from a polyimide obtained by combination of a tetracarboxylic dianhydride and a diamine, having a glass transition temperature of 240° C. or higher, or without a distinct transition point at 300° C. or higher.

From the viewpoint of heat resistance and dimensional stability under high temperature, the porous polyimide film of the invention is preferably a porous polyimide film comprising one of the following aromatic polyimides.

(i) An aromatic polyimide comprising at least one tetracarboxylic acid unit selected from the group consisting of biphenyltetracarboxylic acid units and pyromellitic acid units, and an aromatic diamine unit, (ii) an aromatic polyimide comprising a tetracarboxylic acid unit and at least one type of aromatic diamine unit selected from the group consisting of benzenediamine units, diaminodiphenyl ether units and bis(aminophenoxy)phenyl units, and/or, (iii) an aromatic polyimide comprising at least one type of tetracarboxylic acid unit selected from the group consisting of biphenyltetracarboxylic acid units and pyromellitic acid units, and at least one type of aromatic diamine unit selected from the group consisting of benzenediamine units, diaminodiphenyl ether units and bis(aminophenoxy)phenyl units.

While not restrictive, the porous polyimide film for use in the method of the invention may be a porous polyimide film with a multilayer structure, having at least two surface layers (A-surface and B-surface), and a macro-void layer sandwiched between the two surface layers. Preferably, the porous polyimide film is a porous polyimide film wherein the macro-void layer has a partition bonded to the surface layers (A-surface and B-surface) and a plurality of macro-voids with mean pore sizes of 10 to 500 μm in the planar direction of the film, surrounded by the partition and the surface layers (A-surface and B-surface), wherein the macro-void layer partition and the surface layers (A-surface and B-surface) each have thicknesses of 0.01 to 20 μm, with a plurality of pores with mean pore sizes of 0.01 to 100 μm, the pores being optionally communicating with each other, and also having a partial or total multilayer structure in communication with the macro-voids, where the total film thickness is 5 to 500 μm and the porosity is 40% or greater and less than 95%.

The total film thickness of the porous polyimide film used for the invention is not limited, but may be 20 to 75 μm according to one mode. Differences in the film thickness may be observed as differences in cell growth rate, cell morphology, cell saturation within the plate, and the like.

According to the invention, when the porous polyimide film used has two different surface layers (A-surface and B-surface), and a macro-void layer sandwiched between the two surface layers, the mean pore size of the holes in the A-surface may differ from the mean pore size of the holes in the B-surface. Preferably, the mean pore size of the holes in the A-surface is smaller than the mean pore size of the holes in the B-surface. More preferably, the mean pore size of the holes in the A-surface is smaller than the mean pore size of the holes in the B-surface, with the mean pore size of the holes in the A-surface being 0.01 to 50 μm, 0.01 μm to 40 μm, 0.01 μm to 30 μm, 0.01 μm to 20 μm or 0.01 μm to 15 μm, and the mean pore size of the holes in the B-surface being 20 μm to 100 μm, 30 μm to 100 μm, 40 μm to 100 μm, 50 μm to 100 μm or 60 μm to 100 μm. Most preferably, the A-surface of the porous polyimide film is a mesh structure having small holes with a mean pore size of no greater than 15 μm, such as 0.01 μm to 15 μm, and the B-surface is a large-hole structure with a mean pore size of 20 μm or greater, such as 20 μm to 100 μm.

The total film thickness of the porous polyimide film used for the invention can be measured using a contact thickness gauge.

The mean pore size of the surface of the porous polyimide film can be determined by measuring the pore area of 200 or more open holes from a scanning electron micrograph of the porous film surface, and calculating the mean diameter from the average value for the pore areas according to the following formula (1), assuming the pore shapes to be circular.

[Mathematical Formula 1]

$$\text{Mean pore size} = 2 \times \sqrt{(Sa/\pi)} \quad (1)$$

(wherein Sa represents the average value for the pore areas)

The porosity of the porous polyimide film used for the invention can be determined by measuring the film thickness and mass of the porous film cut out to a prescribed size, and performing calculation from the basis weight according to the following formula (2).

[Mathematical Formula 2]

$$\text{Porosity (\%)} = (1 - w/(S \times d \times D)) \times 100 \quad (2)$$

(wherein S represents the area of the porous film, d represents the total film thickness, w represents the measured mass, and D represents the polyimide density, the polyimide density being defined as 1.34 g/cm$^3$.)

For example, the porous polyimide films described in International Patent Publication No. WO2010/038873, Japanese Unexamined Patent Publication No. 2011-219585 and Japanese Unexamined Patent Publication No. 2011-219586 may also be used in the method of the invention.

The cells that have been seeded on the surface of the porous polyimide film can stably grow and proliferate on the surface and/or in the interior of the film. The cells may be in a variety of different forms, depending on the location of growth and proliferation in the film. According to one mode of the invention, growth may be carried out while moving the surface and interior of the porous polyimide film and changing the form, depending on the type of cell.

Naturally, the porous polyimide film to which cells are applied in the method of the invention is preferably in a state including no cells other than those that are to be applied, i.e. a sterilized state. The method of the invention preferably includes a step of pre-sterilizing the porous polyimide film. A porous polyimide film has very excellent heat resistance and is lightweight, allows free selection of the shape and size, and is easy to treat for sterilization. Any desired sterilization treatment may be conducted, such as dry heat sterilization, steam sterilization, sterilization with a disinfectant such as ethanol, or electromagnetic wave sterilization using ultraviolet rays or gamma rays.

4. Cell Culturing and Culturing Volume

FIG. 1 shows a model diagram of cell culturing using a porous polyimide film. FIG. 1 serves merely for illustration and the elements are not drawn to their actual dimensions. In the method of the invention, application of cells and culturing are carried out on a porous polyimide film, thereby allowing culturing of large volumes of cells to be accomplished since large numbers of cells grow on the multisided connected pore sections on the inside, and the surfaces on the porous polyimide film. Moreover, in the method of the invention, it is possible to culture large volumes of cells while drastically reducing the amount of medium used for cell culturing compared to the prior art. For example, large volumes of cells can be cultured even when all or a portion of the porous polyimide film is not in contact with the liquid phase of the cell culture medium. Also, the total volume of the cell culture medium in the cell culturing vessel, with respect to the total porous polyimide film volume including the cell survival zone, can be significantly reduced below that of methods of the prior art.

Throughout the present specification, the volume of the porous polyimide film without cells, occupying the space including the volume between the interior gaps, will be referred to as the "apparent porous polyimide film volume" (the state shown at the left in FIG. 1). In the state where the cells are applied to the porous polyimide film and the cells have been supported on the surface and the interior of the porous polyimide film, the total volume of the porous polyimide film, the cells and the medium that has wetted the porous polyimide film interior, which is occupying the space therein, will be referred to as the "porous polyimide film volume including the cell survival zone" (the state shown at the right in FIG. 1). When the porous polyimide film has a film thickness of 25 μm, the porous polyimide film volume including the cell survival zone is a value of at maximum about 50% larger than the apparent porous polyimide film volume. In the method of the invention, a plurality of porous polyimide films may be housed in a single cell culturing vessel for culturing, in which case the total sum of the porous polyimide film volume including the cell survival zone for each of the plurality of porous polyimide films supporting the cells may be referred to simply as the "total sum of the porous polyimide film volume including the cell survival zone".

Using the method of the invention, cells can be satisfactorily cultured even under conditions in which the total volume of the cell culture medium in the cell culturing vessel is 10,000 times or less of the total sum of the porous polyimide film volume including the cell survival zone. Moreover, cells can be satisfactorily cultured even under conditions in which the total volume of the cell culture medium in the cell culturing vessel is 1000 times or less of the total sum of the porous polyimide film volume including the cell survival zone. In addition, cells can be satisfactorily cultured even under conditions in which the total volume of the cell culture medium in the cell culturing vessel is 100 times or less of the total sum of the porous polyimide film volume including the cell survival zone. Cells can also be satisfactorily cultured even under conditions in which the total volume of the cell culture medium in the cell culturing vessel is 10 times or less of the total sum of the porous polyimide film volume including the cell survival zone.

In other words, according to the invention the space (vessel) used for cell culturing can be reduced to an absolute minimum, compared to a conventional two-dimensional cell culturing apparatus. Furthermore, when it is desired to increase the number of cells cultured, the cell culturing volume can be flexibly increased by a convenient procedure including increasing the number of layered porous polyimide films. In a cell culturing apparatus comprising a porous polyimide film to be used for the invention, the space (vessel) in which cells are cultured and the space (vessel) in which the cell culture medium is stored can be separate, and the necessary amount of cell culture medium can be prepared according to the number of cells to be cultured. The space (vessel) in which the cell culture medium is stored can be increased or decreased according to the purpose, or it may be a replaceable vessel, with no particular restrictions.

For example, in the culturing conditions of Example 1, culturing was carried out using 4 ml of medium with human skin fibroblasts applied to 50 porous polyimide films each having a 1.4 cm square shape and a 25 μm film thickness (total sum of porous polyimide film volume including the cell survival zone: ~0.25 cm$^3$). These are conditions in which the total volume of the cell culture medium in the cell culturing vessel was about 16 times the total sum of the porous polyimide film volume including the cell survival zone. As a result, mass culturing could be carried out, in which the number of cells where all of the cells were evenly dispersed in the cell culture medium reached a number exceeding $2.5 \times 10^6$ per milliliter of medium, despite the fact that the cells were a non-established human adherent cell line.

Throughout the present specification, "mass culturing of cells" refers to culturing in which, for example, the number of cells in the cell culturing vessel after culturing using the porous polyimide film reaches $1.0 \times 10^5$ or more, $1.0 \times 10^6$ or more, $2.0 \times 10^6$ or more, $5.0 \times 10^6$ or more, $1.0 \times 10^7$ or more, $2.0 \times 10^7$ or more, $5.0 \times 10^7$ or more, $1.0 \times 10^8$ or more, $2.0 \times 10^8$ or more, $5.0 \times 10^8$ or more, $1.0 \times 10^9$ or more, $2.0 \times 10^9$ or more, or $5.0 \times 10^9$ or more, per milliliter of medium, assuming all of the cells evenly disperse in the cell culture medium in the cell culturing vessel. The method used to count the number of cells in the cell culturing vessel after culturing using the porous polyimide film, when the cells are evenly dispersed in the cell culture medium in the cell culturing vessel, may be any publicly known method. For example, a cell counting method using CCK8 may be suitably used, as in the method employed in Example 1. Specifically, a Cell Counting Kit 8 (a solution reagent, commercially available from Dojindo Laboratories, Kumamoto, Japan) (hereunder referred to as "CCK8") may be used to count the number of cells in ordinary culturing without using a porous polyimide film, and the correlation coefficient between the absorbance and the actual cell count determined. After then applying the cells, the cultured porous polyimide film may be transferred to CCK8-containing medium and stored in an incubator of 1 to 3 hours, and then the supernatant extracted and its absorbance measured at a wavelength of 480 nm, and the cell count determined from the previously calculated correlation coefficient.

When animal cells are used, "mass culturing of cells" may refer to culturing in which the number of cells in the cell culturing vessel after culturing using the porous polyimide film reaches $1.0 \times 10^5$ or more, $1.0 \times 10^6$ or more, $2.0 \times 10^6$ or more, $5.0 \times 10^6$ or more, $1.0 \times 10^7$ or more, $2.0 \times 10^7$ or more or $5.0 \times 10^7$ or more, per milliliter of medium, assuming that all of the cells are evenly dispersed in the cell culture medium in the cell culturing vessel.

When fibroblasts such as human skin fibroblasts are used, "mass culturing of cells" may refer to culturing in which the number of cells in the cell culturing vessel after culturing using the porous polyimide film reaches $1.0 \times 10^5$ or more, $1.0 \times 10^6$ or more, $2.0 \times 10^6$ or more, $5.0 \times 10^6$ or more, $1.0 \times 10^7$ or more, $2.0 \times 10^7$ or more or $5.0 \times 10^7$ or more, per milliliter of medium, assuming that the cells are evenly dispersed in the cell culture medium in the cell culturing vessel.

When CHO cells are used, "mass culturing of cells" may refer to culturing in which the number of cells in the cell culturing vessel after culturing using the porous polyimide film reaches $1.0 \times 10^5$ or more, $1.0 \times 10^6$ or more, $2.0 \times 10^6$ or more, $5.0 \times 10^6$ or more, $1.0 \times 10^7$ or more, $2.0 \times 10^7$ or more or $5.0 \times 10^7$ or more, per milliliter of medium, assuming that all of the cells are evenly dispersed in the cell culture medium in the cell culturing vessel.

When HeLa cells are used, "mass culturing of cells" may refer to culturing in which the number of cells in the cell culturing vessel after culturing using the porous polyimide film reaches $1.0 \times 10^5$ or more, $1.0 \times 10^6$ or more, $2.0 \times 10^6$ or more, $5.0 \times 10^6$ or more, $1.0 \times 10^7$ or more, $2.0 \times 10^7$ or more or $5.0 \times 10^7$ or more, per milliliter of medium, assuming that all of the cells are evenly dispersed in the cell culture medium in the cell culturing vessel.

From a different viewpoint, "mass culturing of cells" refers to culturing in which, for example, the number of cells per square centimeter of the porous polyimide film after culturing using the porous polyimide film reaches $1.0 \times 10^5$ or more, $2.0 \times 10^5$ or more, $1.0 \times 10^6$ or more, $2.0 \times 10^6$ or more, $5.0 \times 10^6$ or more, $1.0 \times 10^7$ or more, $2.0 \times 10^7$ or more, $5.0 \times 10^7$ or more, $1.0 \times 10^8$ or more, $2.0 \times 10^8$ or more or $5.0 \times 10^8$ or more. The number of cells per square centimeter of porous polyimide film can be appropriately measured using a publicly known method, such as with a cell counter.

When animal cells are used, mass culturing of cells may refer to culturing to a cell count of $1.0 \times 10^5$ or more, $2.0 \times 10^5$ or more, $1.0 \times 10^6$ or more, $2.0 \times 10^6$ or more, $5.0 \times 10^6$ or more, $1.0 \times 10^7$ or more, $2.0 \times 10^7$ or more, or $5.0 \times 10^7$ or more.

The definition of "mass culturing" for the purpose of the present specification is, growth of a large number of cells per square centimeter of the porous polyimide film, as well as culturing in which the cells adhering to the porous polyimide film make up at least 80% of the total number of cells, without the cells on the sheet forming spheroid-like cell aggregation. This is an important condition for carrying out stable mass culturing, and it means stable culturing of a cell population having a scaffold for stable growth, while supplying sufficient medium nutrients and oxygen onto and into the porous polyimide film, without aggregation between the cells that may elicit clumping or necrosis.

3. Cell Culturing System and Culturing Conditions

In the method of the invention, the cell culturing system and culturing conditions may be set as appropriate according to the type of cells used. Culturing methods suited for various cells including animal cells, plant cells and bacteria are publicly known, and a person skilled in the art may carry out culturing of cells suited for the porous polyimide film, using any publicly known method. The cell culture medium may also be prepared as appropriate for the type of cells.

Cell culture methods and cell culture media for animal cells may be found in the Cell Culture Media Catalog of Lonza Group, Ltd., for example. Cell culture methods and cell culture media for plant cells may also be found in the Plant Tissue Culturing Media Series by Wako Corp. Japan, for example. Cell culture methods and cell culture media for bacteria may also be found in the General Bacterial Media Catalog of BD Corp., for example. The cell culture medium to be used in the method of the invention may be in any form such as a liquid medium, semi-solid medium or solid medium. Also, a liquid medium in droplet form may be sprayed into the cell culturing vessel to contact the medium with the cell-supporting porous polyimide film.

The cell culture using a porous polyimide film may also be combined with another suspension culture support such as a microcarrier, cellulose sponge or the like.

The method of the invention is not particularly restricted in terms of the form and scale of the system used for the culturing, and any scale from cell culturing dish to a flask, plastic bag, test tube or large tank may be used, as appropriate. These include, for example, Cell Culture Dish by BD Falcon, and Nunc Cell Factory by Thermo Scientific. By using a porous polyimide film according to the invention, it has become possible to carry out culturing even of cells that have not been capable of natural suspension culture, using an apparatus intended for suspension culture, in a state similar to suspension culturing. The apparatus for suspension culture that is used may be, for example, a spinner flask or rotating culturing flask by Corning, Inc. As an environment allowing a similar function to be obtained, there may be used a hollow fiber culturing system such as the FiberCell® System by Veritas.

The culturing in the method of the invention may be carried out in a manner with continuous circulation such as continuous addition and recovery of the medium on the porous polyimide film, or exposure of the porous polyimide film sheet to air using an open apparatus.

Cell culturing according to the invention may be carried out in a system in which a cell culture medium is continuously or intermittently supplied to a cell culturing vessel from cell culture medium supply means installed outside of the cell culturing vessel. The system may be such that the cell culture medium is circulated between the cell culture medium supply means and the cell culturing vessel.

When the cell culturing is carried out in a system in which the cell culture medium is continuously or intermittently supplied to the cell culturing vessel from cell culture medium supply means installed outside of the cell culturing vessel, the system may be a cell culturing apparatus including a culturing unit which is the cell culturing vessel, and a culture medium-supply unit which is the cell culture medium supply means, wherein the culturing unit is a culturing unit that houses one or more porous polyimide films to support cells, and that comprises a culture medium supply port and a culture medium discharge port, and the culture medium-supply unit is a culture medium-supply unit comprising a culture medium housing vessel, a culture medium supply line, and a liquid conveyance pump that conveys the medium continuously or intermittently through the culture medium supply line, the first end of the culture medium supply line contacting the medium in the culture medium housing vessel, and the second end of the culture medium supply line being in communication with the culturing unit interior via the culture medium supply port of the culturing unit.

In the cell culturing apparatus, the culturing unit may be a culturing unit that does not comprise an air supply port and an air discharge port, or it may be a culturing unit that comprises an air supply port and an air discharge port. Even if the culturing unit does not comprise an air supply port and air discharge port, the oxygen, etc. necessary for cell culturing is adequately supplied to the cells through the medium. Furthermore, in the cell culturing apparatus described above, the culturing unit may further comprise a culture medium discharge line, the first end of the culture medium discharge line being connected to the culture medium housing vessel, the second end of the culture medium discharge line being in communication with the culturing unit interior via the culture medium discharge port of the culturing unit, and the medium being able to circulate through the culture medium-supply unit and the culturing unit.

Figure 2:
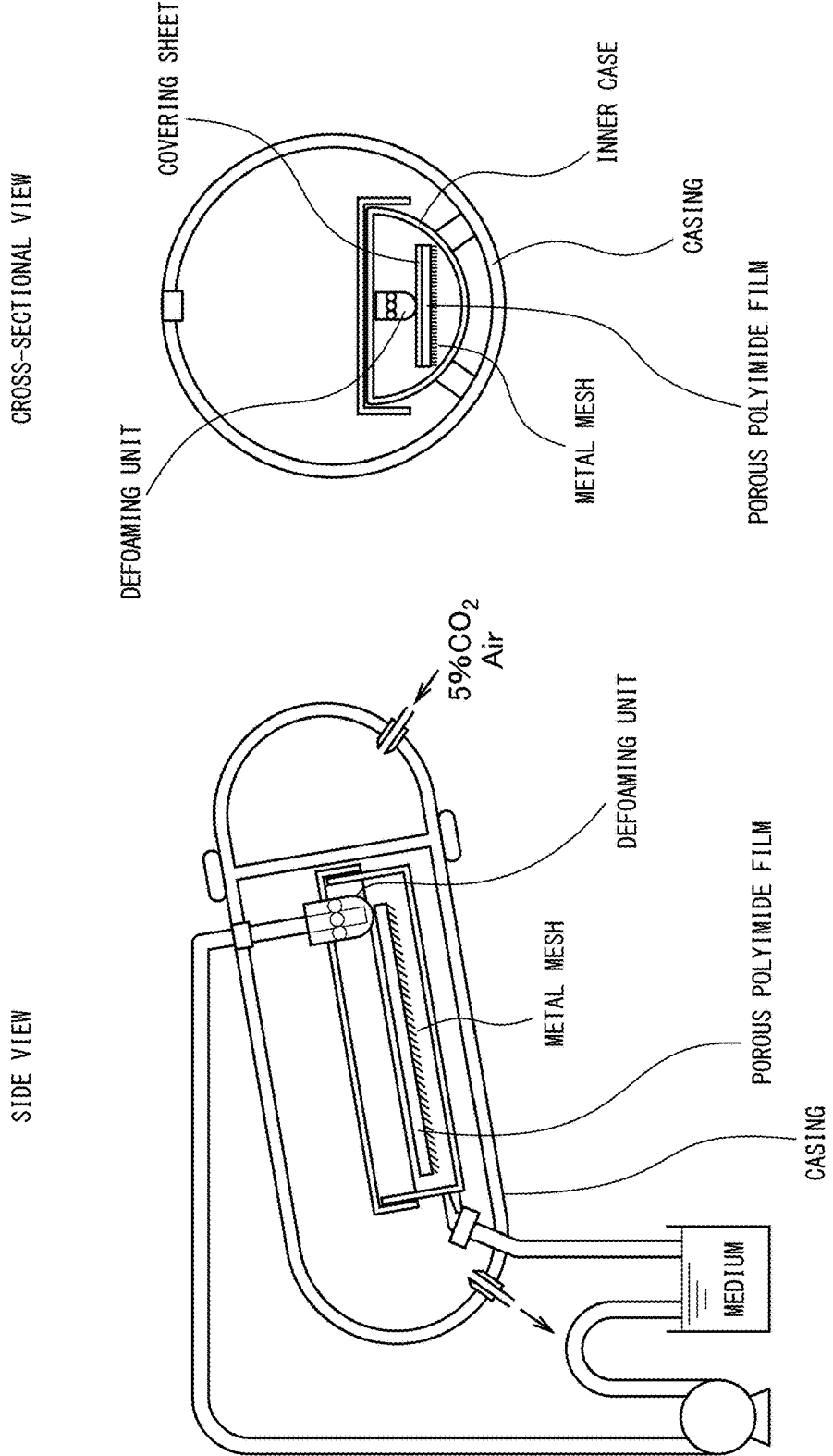
FIG. 2 shows an example of a cell culturing apparatus.

An example of a cell culturing apparatus, as a cell culturing system, is shown in FIG. 2, although the cell culturing system to be used for the object of the invention is not limited to such an apparatus.

II. Cell Culturing Apparatus

The invention further relates to a cell culturing apparatus including:

a culturing unit that houses one or more porous polyimide films to support cells, and that comprises a culture medium supply port and a culture medium discharge port, and a culture medium-supply unit comprising a culture medium housing vessel, a culture medium supply line, and a liquid conveyance pump that conveys the medium continuously or intermittently through the culture medium supply line, the first end of the culture medium supply line contacting the medium in the culture medium housing vessel, and the second end of the culture medium supply line being in communication with the culturing unit interior via the culture medium supply port of the culturing unit. The entire content of International Application Number PCT/JP2014/070407 is incorporated herein by reference.

The present invention also relates to a cell culturing apparatus for use in the culturing method of the invention, the apparatus including a porous polyimide film. In the cell culturing apparatus of the invention, the porous polyimide film may be used in a fixed state, or it may be used in a floating state in the cell culture medium, and it may be either placed in the medium or exposed from the medium. In the cell culturing apparatus, two or more porous polyimide films may be layered either above and below or left and right. The layered aggregates or cluster may be either placed in the medium or exposed from the medium.

The cell culturing apparatus of the invention may be in any desired form so long as it includes the porous polyimide film. For example, any of the aforementioned cell culturing systems to be used for the mass culturing method of the invention may be used as the cell culturing apparatus for the invention.

In the cell culturing apparatus of the invention, the porous polyimide film may be used as a single film in a flat or folded form, or two or more porous polyimide films may be layered above and below or folded and layered. The method of layering the porous polyimide films is not restricted, and the layering may be with the A-surfaces and B-surfaces placed together.

The cell culture medium to be used in the method of the invention (this may be referred to simply as "medium" throughout the present specification) may be in any form such as a liquid medium, semi-solid medium or solid medium, but it is preferably used as a liquid medium. Also, a liquid medium in mist or droplet form may be sprayed into the cell culturing vessel to contact the medium with the cell-supporting porous polyimide film.

The cell culture using a porous polyimide film may also be combined with another suspension culture support such as a microcarrier, cellulose sponge or the like.

The cell culturing apparatus of the invention includes a culturing unit that houses one or more porous polyimide films to support the cells, and a culture medium-supply unit.

In the culturing unit interior, the porous polyimide film may be used in a fixed state, or it may be used in a floating state in the cell culture medium, and it may be either placed in the medium or exposed from the medium. In the cell culturing apparatus, two or more porous polyimide films may be layered either above and below or left and right. The layered aggregates or cluster may be either placed in the medium or exposed from the medium.

The culturing unit comprises a culture medium supply port and a culture medium discharge port. The culturing unit may be one that does not comprise an air supply port, an air discharge port and an oxygen exchange membrane. According to the invention, the amount of medium used is extremely minimal, and the porous polyimide film used as the culture support can be exposed to a gas phase, thereby allowing oxygen supply to the cells to be adequately accomplished by diffusion.

According to the invention, therefore, there is no particular need for an oxygen supply apparatus or a gas exchange mechanism. Naturally, the culturing unit may be one that does comprise an air supply port and an air discharge port, or an oxygen exchange membrane. The air supply port and the air discharge port may be a 5% $CO_2$ gas-containing air supply port and a 5% $CO_2$ gas-containing air discharge port.

The culturing unit may be one without means for agitating the porous polyimide film. This is because, according to the invention, the amount of medium used in the culturing vessel is extremely minimal and the porous polyimide film used as the culture support can be exposed to a gas phase, thereby allowing oxygen supply to the cells to be adequately accomplished by diffusion. Naturally, the culturing unit may be one housing means for agitating the porous polyimide film.

Furthermore, the culturing unit may be one further comprising a culture medium discharge line, the first end of the culture medium discharge line being connected to the culture medium housing vessel, the second end of the culture medium discharge line being in communication with the culturing unit interior via the culture medium discharge port of the culturing unit, and the medium being able to circulate through the culture medium-supply unit and the culturing unit. In this case, continuous supply of medium can be made, without requiring frequent supply of medium or exchange of the medium.

Also, the culturing unit may be one further comprising a culture medium discharge line, the first end of the culture medium discharge line being connected to the culture medium collecting unit, the second end of the culture medium discharge line being in communication with the culturing unit interior via the culture medium discharge port of the culturing unit, and the discharged medium being recoverable in the culture medium collecting unit. This mode can be effectively used when, for example, it is desired to recover a substance produced by cells from a discharged medium.

The cell culturing apparatus of the invention includes a culture medium-supply unit. The culture medium-supply unit comprises a culture medium housing vessel, a culture medium supply line, and a liquid conveyance pump that conveys the medium continuously or intermittently through the culture medium supply line, the first end of the culture medium supply line contacting the medium in the culture medium housing vessel, and the second end of the culture medium supply line being in communication with the culturing unit interior via the culture medium supply port of the culturing unit.

The cell culturing apparatus of the invention may be one further including means for shaking the culturing unit. The means for shaking the culturing unit is not particularly restricted so long as a suitable degree of shaking can be externally applied to the cell culturing, and an example is a shaking apparatus such as a Multishaker.

Figure 12:
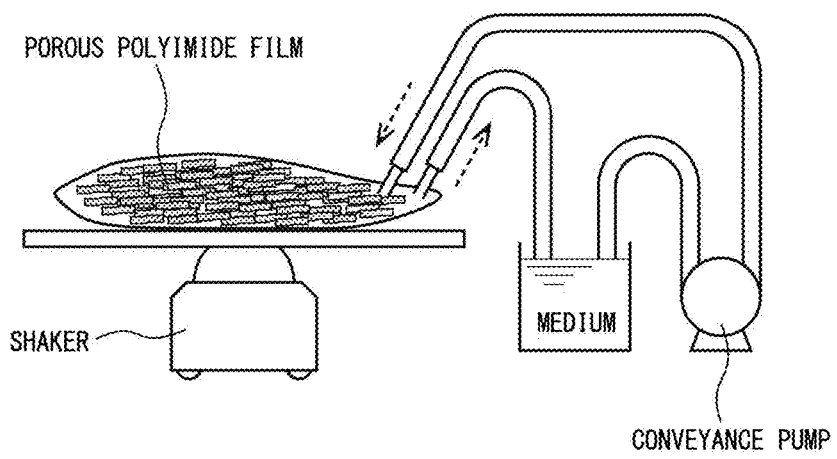
FIG. 12 shows an example of a cell culturing apparatus using a flexible bag. The cell-seeded porous polyimide films and medium are placed in an oxygen-permeable single use culture bag, and the culture medium supply line and discharge line are installed. The entire apparatus is placed in a 5% $CO_2$-supply incubator at 37° C., and culturing is performed.
Figure 13:
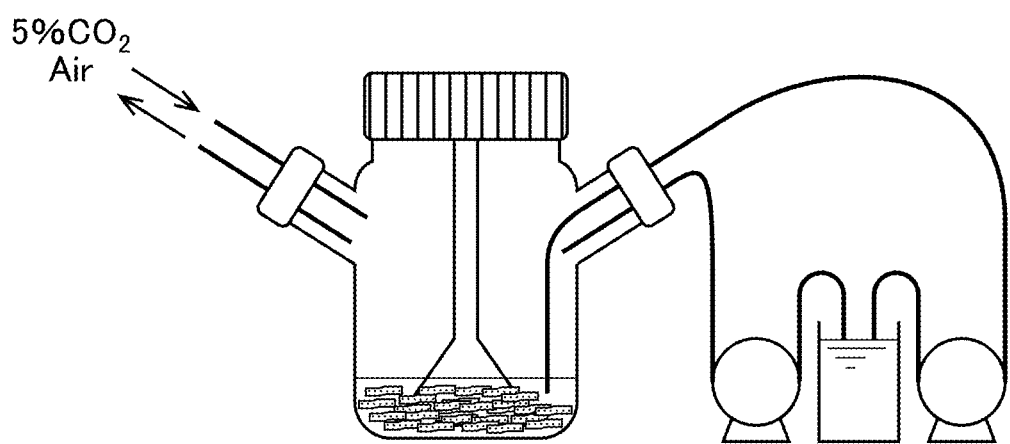
FIG. 13 shows an example of a cell culturing apparatus using a spinner flask. The cell-seeded porous polyimide films and medium are placed in the spinner flask, and the culture medium supply line and discharge line are installed. A 5% $CO_2$-containing air line is connected, the entire apparatus is placed in an incubator at 37° C., and culturing is performed.

The culturing unit in the cell culturing apparatus of the invention may be made of any material in any form so long as it has the aforementioned elements. The porous polyimide film may be housed and used in a commercially available culturing vessel either with or without modification of the vessel. Examples of commercially available culturing vessels include gas-impermeable or -permeable flexible bags such as plastic bags, and spinner flasks, with no limitation to these. FIG. 12 shows an example of a cell culturing apparatus wherein the culturing unit comprises a flexible bag, and FIG. 13 shows an example of a cell culturing apparatus wherein the culturing unit comprises a spinner flask.

In the cell culturing apparatus of the invention, the one or more porous polyimide films are mounted on a rigid body inclined at an angle of no greater than 45° with respect to the horizontal, the second end of the culture medium supply line is installed so that the medium is supplied from a region near the top end of the porous polyimide film, and the second end of the culture medium discharge line is installed so that the medium is discharged from a region near the bottom end of the porous polyimide film. An example of such a cell culturing apparatus is shown in FIG. 2. A rigid body may be inclined at an angle of no greater than 40°, no greater than 35°, no greater than 30°, no greater than 25°, no greater than 20°, no greater than 15°, no greater than 10° or no greater than 5°, with respect to the horizontal. The inclination angle of the rigid body may be appropriately optimized depending on the type of cells to be cultured, the number of cells seeded, the culture growth rate and the oxygen requirement, or it may be varied periodically. The material of the rigid body is not particularly restricted so long as it allows the porous polyimide film to be stably supported, and a metal mesh such as stainless steel may be mentioned as an example.

In the cell culturing apparatus, the second end of the culture medium supply line may be installed so that the medium is supplied from a region near the top end of the porous polyimide film, and the second end of the culture medium discharge line may be installed so that the medium is discharged from a region near the bottom end of the porous polyimide film. Here, "near the top end of the porous polyimide film" means that a position of the porous polyimide film which is the highest end from among approximately three equal portions thereof in the direction of the incline of the rigid body when the porous polyimide film is mounted on the rigid body, and to which the medium can be applied. Also, "near the bottom end of the porous polyimide film" means a portion of the porous polyimide film which is the lowest end from among approximately three equal portions thereof in the direction of the incline of the rigid body when the porous polyimide film is mounted on the rigid body, and from which the medium can be discharged.

In the cell culturing apparatus, the one or more porous polyimide films and the rigid body may be housed in a housing, the housing being in turn housed in the culturing unit interior. The material and form of the housing may be determined as appropriate according to the purpose.

Figure 10:
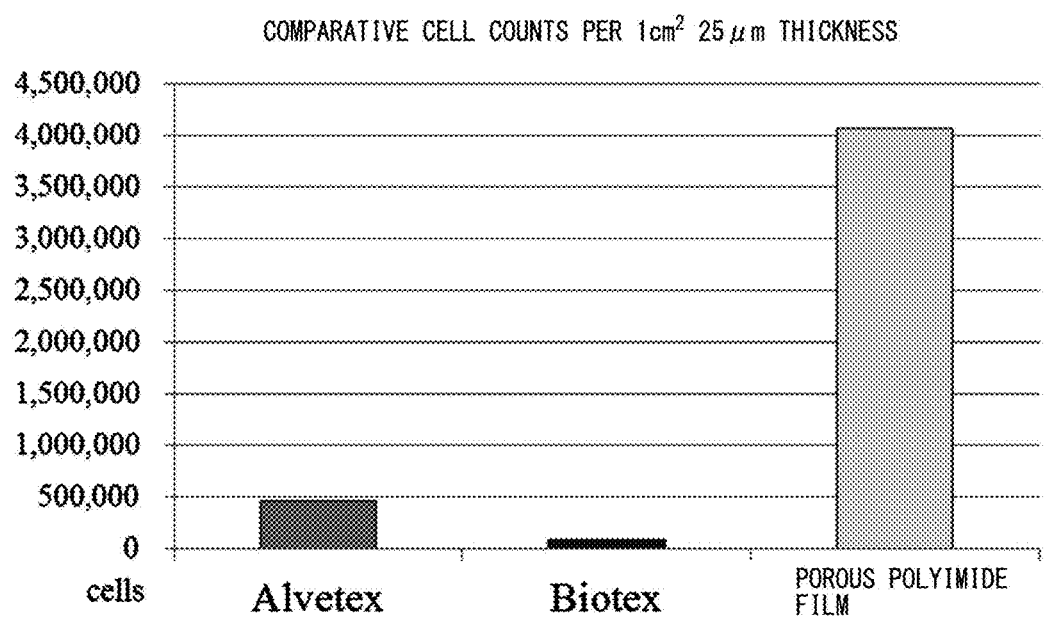
FIG. 10 is a graph showing culturing results for gene recombinant CHO-K1 cells using porous polyimide films and a commercially available three-dimensional culture scaffold.

The construction of the cell culturing apparatus may be such that the one or more porous polyimide films and the rigid body that mounts the one or more porous polyimide films are provided in a plurality, as shown in FIG. 10. This will allow each level of porous polyimide film to have medium under basically the same conditions, so that the culturing conditions can be consistent at each level even with mass culturing of the cells.

In the cell culturing apparatus, a porous sheet having a larger mean pore size than the one or more porous polyimide films may be further mounted so as to cover all or a portion of the top surface of the porous polyimide film. The porous sheet used may be any one so long as it has a larger mean pore size than the porous polyimide film, and for example, a nonwoven fabric, gauze or sponge may be suitably used. If a porous sheet with a larger mean pore size than the porous polyimide film is mounted on the porous polyimide film, drift current of medium, and especially liquid medium, flowing on the surface of the porous polyimide film can be minimized, allowing the medium to be homogeneously applied onto the surface of the porous polyimide film and thus increasing the culture efficiency.

In the cell culturing apparatus, a defoaming unit may be further installed near the second end of the culture medium supply line. Here, "near the second end of the culture medium supply line" means a location such that the defoaming unit can capture air bubbles produced when the medium has been supplied onto the porous polyimide film. By installing a defoaming unit, it is possible to homogeneously apply the medium onto the porous polyimide film surface, to allow the culture efficiency to be further increased.

The cell culturing apparatus of the invention can greatly reduce the volume of culture medium used in the culturing tank in the cell culturing apparatus, regardless of which of the aforementioned modes is employed, thereby contributing to downsizing and space reduction of the culturing apparatus. All or some of the one or more porous polyimide films may be wetted with the medium, for example. Also, all or some of the one or more porous polyimide film surfaces may be out of contact with the liquid phase of the medium. A state in which all or some of the surfaces of the one or more porous polyimide films are not in contact with the liquid phase of the medium, may be a state in which all or some of the surfaces of the one or more porous polyimide films are exposed to a gas phase. In the cell culturing apparatus of the invention, the medium is supplied continuously or intermittently to the porous polyimide films, and therefore a wetted state is maintained, with the medium in all or some of the holes present in the porous polyimide films.

The cell culturing apparatus of the invention allows mass culturing of cells while drastically reducing the amount of medium used for cell culturing compared to methods of the prior art, and therefore the total volume of the cell culture medium in the culturing unit with respect to the total sum of the porous polyimide film volume including the cell survival zone, can be significantly reduced below that in methods of the prior art.

Throughout the present specification, the volume of the porous polyimide film without cells, that occupies the space including the volume between the interior gaps, will be referred to as the "apparent porous polyimide film volume". In the state where the cells are applied to the porous polyimide film and the cells have been supported on the surface and the interior of the porous polyimide film, the total volume of the porous polyimide film, the cells and the medium that has wetted the porous polyimide film interior, which is occupying the space therein, will be referred to as the "porous polyimide film volume including the cell survival zone". When the porous polyimide film has a film thickness of 25 µm, the porous polyimide film volume including the cell survival zone is a value of at maximum about 50% larger than the apparent porous polyimide film volume. In the method of the invention, a plurality of porous polyimide films may be housed in a single culturing unit for culturing, in which case the total sum of the porous polyimide film volume including the cell survival zone for each of the plurality of porous polyimide films supporting the cells may be referred to simply as the "total sum of the porous polyimide film volume including the cell survival zone".

Using the method of the invention, cells can be satisfactorily cultured even under conditions in which the total volume of the cell culture medium in the culturing unit is 10,000 times or less, 1000 times or less, 100 times or less, 10 or less or 5 times or less, of the total sum of the porous polyimide film volume including the cell survival zone.

The present invention further relates to a cell culturing method that includes installing the aforementioned cell culturing apparatus in an incubator and culturing cells.

The incubator used may be any one that can maintain a temperature suited for culturing of cells. An incubator that can adjust the humidity and $CO_2$ concentration, in addition to the temperature, may also be used. When using ordinary animal cells, an incubator that can supply 5% $CO_2$ to the cell culturing apparatus may be used.

III. Kit for use in Cell Culturing Method

The present invention also relates to a kit for use in the cell culturing method of the invention, the apparatus including a porous polyimide film.

The kit of the invention may include constituent elements necessary for cell culturing in addition to the porous polyimide film, as appropriate. This includes, for example, the cells to be applied to the porous polyimide film, the cell culture medium, the continuous culture medium-supply apparatus, the continuous culture medium-circulating apparatus, the scaffold or module for support of the porous polyimide film, the cell culturing apparatus, and the kit instruction manual.

While not restrictive, one mode includes a package containing either one or a plurality of sterilized porous polyimide films stored in a transparent pouch, in a form allowing their use for cell culturing, or a kit having a sterile liquid encapsulated together with a porous polyimide film in the same pouch, in the form of an integrated film/liquid allowing efficient suction seeding.

IV. Method for Collection of Substance Produced by Cells

The present invention further relates to a method for collection of a substance produced by cells, the method including installing the aforementioned cell culturing apparatus in an incubator and culturing cells, and continuously or intermittently collecting the medium that has contacted with the cells. According to the method of the invention the cells are held in a porous polyimide film, and thus there is no need to employ a centrifugal separation procedure or filter for removal of the cells or cell-produced debris as in the prior art, and the culture supernatant alone may be recovered.

V. Use of Cell Culturing Apparatus

The present invention also relates to the use of the aforementioned cell culturing apparatus for culturing of cells. The invention still further relates to the use of the aforementioned cell culturing apparatus for collection of a substance produced by cells.

The present invention will now be explained in greater detail by examples. It is to be understood, however, that the invention is not limited to these examples. A person skilled in the art may easily implement modifications and changes to the invention based on the description in the present specification, and these are also encompassed within the technical scope of the invention. Unless otherwise specified, the term "porous polyimide film" refers to a porous polyimide film with a total film thickness of 25 μm and a porosity of 73%. Each porous polyimide film had at least two different surface layers (A-surface and B-surface), and a macro-void layer sandwiched between the two surface layers. The mean pore size of the holes in the A-surface was 6 μm, and the mean pore size of the holes in the B-surface was 46 μm.

The porous polyimide films used in the following examples were prepared by forming a polyamic acid solution composition including a polyamic acid solution obtained from 3,3',4,4'-biphenyltetracarboxylic dianhydride (s-BPDA) as a tetracarboxylic acid component and 4,4'-diaminodiphenyl ether (ODA) as a diamine component, and polyacrylamide as a coloring precursor, and performing heat treatment at 250° C. or higher.

<Cells and Materials Used>

Human fibroblasts (product code CC-2511 by Lonza)
CHO-K1 (cat. 85051005 by Public Health England)
CHO DP-12 (ATCC CRL-12445)
Human fibroblast medium (product code CC-3132 by Lonza)
CHO-K1 medium (Ham's F-12 087-08335 by Wako Pure Chemical Industries, Ltd.)
CHO DP-12 medium (IMDM 098-06465 by Wako Pure Chemical Industries, Ltd.)
3.5 cm dish (cat. 353001 by Falcon)
20 $cm^2$ dish (cat. 353004 by Falcon)
Cell Counting Kit 8 (CCK8, Dojindo Laboratories CK04)
Cryotube (1.8 ml cat. 377267 by Thermo Fisher Scientific)
2 cm×2 cm sterilized square vessel (cat. 103k by Thermo Fisher Scientific)
Penicillin-Streptomycin-Amphotericin B Suspension (X100) (161-23181 by Wako Pure Chemical Industries, Ltd.)
Microscope, image software LSM 700 by Carl Zeiss, software: ZEN
Human GCSF-producing CHO-K1 cell line A human GCSF (granulocyte colony stimulating factor)-producing CHO-K1 cell line was obtained, from an entrusted business, by the following procedure. The cells used were CHO-K1 (cat. 85051005 by Public Health England). A cell line stably expressing human GCSF was acquired by the following steps.

Procedure (i): Design and production of plasmid carrying introduced neomycin resistance gene and synthetic human GCSF gene Procedure (ii): Mass preparation of transfection grade plasmid Procedure (iii): Creation of transient gene expressing cells Procedure (iv): Creation of stable gene-expressing line, confirmation of expressed gene by Real Time PCR, and single cloning Procedure (v): Confirmation of target protein expression of each clone by ELISA The satisfactory producing cell line #42 was selected from among the obtained cell lines, and used in the following experiment.

Example 1

Mass Culturing of Human Skin Fibroblasts Using Porous Polyimide Film

Human skin fibroblasts were used for seeding in a porous polyimide film, and then mass culturing was carried out in a dish.

After adding 0.5 ml of 2% FBS-containing cell culture medium to a 2 cm×2 cm sterilized square vessel, a sterilized 1.4 cm-square porous polyimide film was immersed therein with the A-surface of the mesh structure or the B-surface of the large-gap structure facing upward. Separately, there was prepared a human skin fibroblast suspension with human skin fibroblasts suspended at $2.1 \times 10^6$ cells per 1 ml of medium (of which $1.9 \times 10^6$ were viable cells and $1.6 \times 10^5$ were dead cells, for a viable cell rate of 92%). The cell suspension was added at 50 μl to the cell culture medium in the square vessel.

Figure 3:
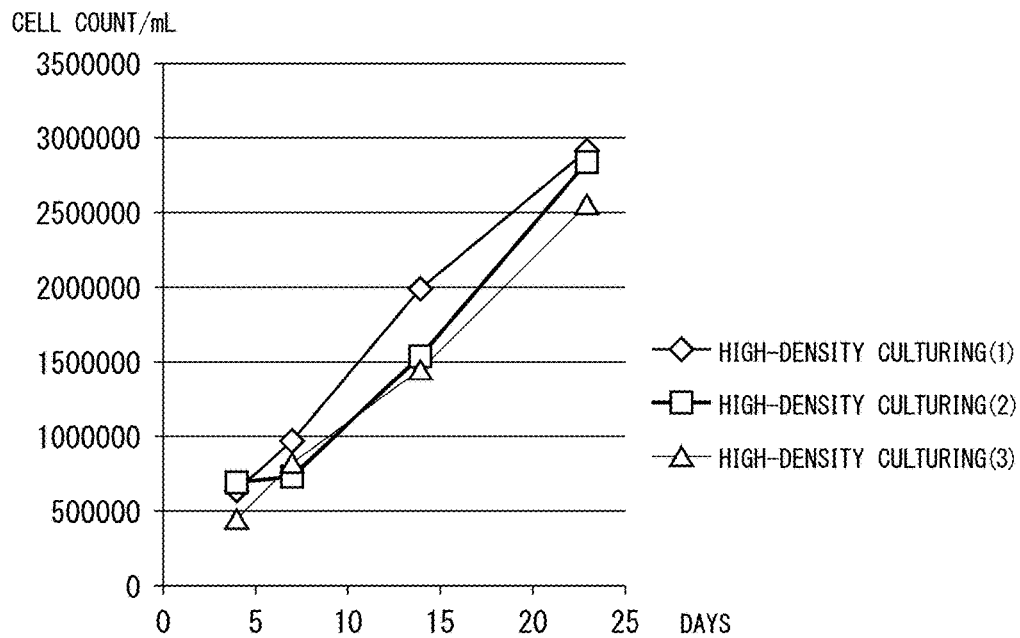
FIG. 3 shows results for mass culturing of human skin fibroblasts using a porous polyimide film.

After culturing for 24 hours in the square vessel, 150 cell-seeded sheets were transferred to three 20 cm² dishes, 50 sheets at a time, 4 ml of medium was added, and culturing was continued. After 4 days, 7 days, 14 days and 23 days, CCK8 was used to measure the cell counts and observe the growth behavior. The results are shown in FIG. 3.

Example 2

Mass Culturing of CHO-K1 Cells Using Porous Polyimide Film

For this example, CHO-K1 cells were used for seeding in a porous polyimide film, and then mass culturing was carried out in a dish.

After adding 0.5 ml of 2% FBS-containing cell culture medium to a 2 cm×2 cm sterilized square vessel, a sterilized 1.4 cm-square porous polyimide film was immersed therein with the A-surface of the mesh structure facing upward. Separately, a CHO-K1 cell suspension was prepared with the CHO-K1 cells suspended at $5.0 \times 10^6$ cells per 4 ml of medium (of which $4.5 \times 10^6$ were viable cells and $4.7 \times 10^5$ were dead cells, for a viable cell rate of 91%). The cell suspension was added at 40 μl to the cell culture medium in the square vessel.

After culturing for 24 hours in the square vessel, 25 cell-seeded sheets were transferred to one 20 cm² dish and collected, 2 ml of medium was added, and culturing was continued. After 11 days, 18 days and 20 days, CCK8 was used to measure the cell count and observe the growth behavior of the cells. Throughout the observation period, at least $1.0 \times 10^7$ per ml of the cells were found to be alive.

TABLE 2

| | Culturing period | | |
|---|---|---|---|
| | 11 days | 18 days | 20 days |
| Cell count/ml | $1.0 \times 10^7$ | $1.6 \times 10^7$ | $1.6 \times 10^7$ |

Example 3

Mass Continuous Culturing of CHO-K1 Cells Using Porous Polyimide Films

For this example, CHO-K1 cells were used for seeding in porous polyimide films, and then mass continuous culturing was carried out using a continuous culturing apparatus.

Ten 4 cm×10 cm sterilized porous polyimide films were subjected to dry heat sterilization, and arranged in a sterilized rectilinear dish. A suspension was prepared including $1.1 \times 10^7$ CHO-K1 cells per 5 ml of medium (of which $1.1 \times 10^7$ were viable cells and $5.0 \times 10^5$ were dead cells, for a viable cell rate of 96%), and 0.5 ml was seeded into each of the previously prepared porous polyimide films. Each suspension placed on the sheets was homogenized with a cell scraper, and the solution was caused to pass through by slightly moving the sheets, thereby seeding the cells into the porous polyimide films. The 10 sheets were layered with their A-surfaces facing upward and placed on a stainless steel metal mesh of the same size, while PE/PP-mixed nonwoven fabric was placed over it, and the aggregate including the cells was set in a plastic case (see FIG. 2). The layered porous polyimide films including the cells were inclined approximately 20° at this time. Medium (Ham's F-12 containing penicillin/streptomycin/amphotericin B (final concentration: penicillin: 100 IU/ml, streptomycin: 0.1 mg/ml, amphotericin B: 0.25 μg/ml), with 10% FBS added) was continuously added from top end of the incline, and circulated from a 150 ml volume medium reservoir at a flow rate of 3 ml/min. The porous polyimide films were present as a mutually bonded aggregate.

After 3 days, the solution of the medium reservoir was discarded, 100 ml of fresh medium solution was added to the medium reservoir, and circulation of the medium was continued for another 2 days. After 5 days from completion of the seeding, the medium circulation was halted and color reaction with CCK8 was used to determine the viable cell count. The total sum of the viable cells on each of the porous polyimide film sheets was $8.9 \times 10^8$.

Figure 4:
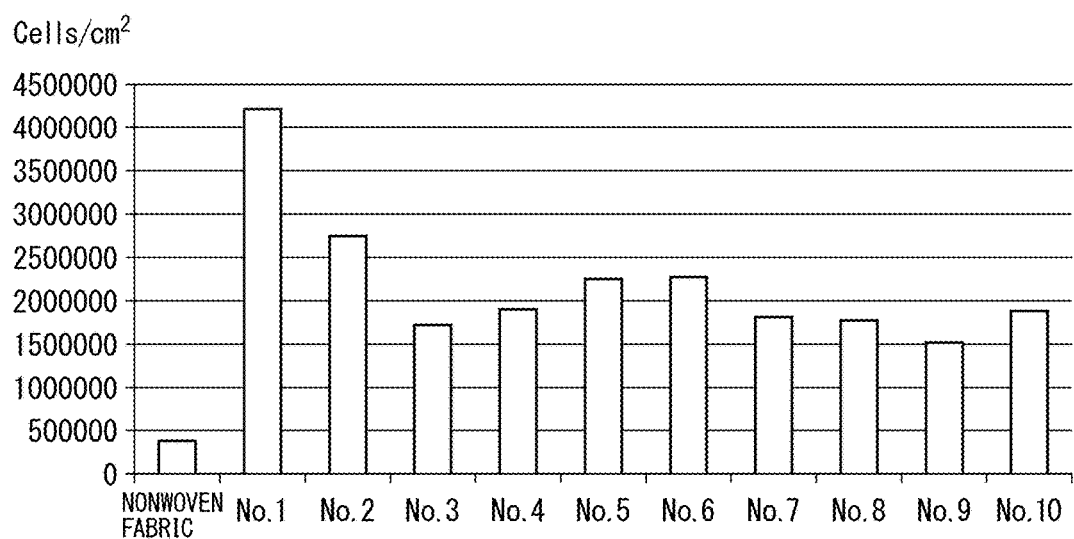
FIG. 4 shows results for mass culturing of CHO-K1 cells using a porous polyimide film.
Figure 5:
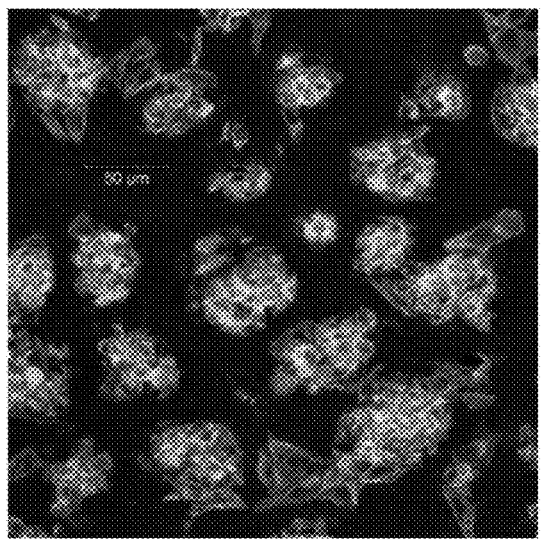
FIG. 5 shows results for mass culturing of CHO-K1 cells using a porous polyimide film.

Assuming the porous polyimide with the film thickness of 25 μm has an increased area of up to 50% of the film thickness, with the top surface and bottom surface, can be applied by the cells and medium, the component volume including the survival region was 1.5 ml, and the viable cell density was $5.9 \times 10^8$ per milliliter. The cell growth on the nonwoven fabric was $1.5 \times 10^7$, and the estimated viable cell density was $3.8 \times 10^6$ per milliliter. FIG. 4 shows the cell count results for each sheet, and for the nonwoven fabric. The numbers in the graph are the numbers of the layered porous polyimide film sheets, counting from the top. The cell-grown porous polyimide films of the uppermost layer (No. 1) and the middle layer (No. 5) were partially cut out and fixed with formalin, staining was performed of the nuclei (DAPI), cell membranes (cell mask) and actin (phalloidin), and then a fluorescent microscope photograph was taken as shown in FIG. 5. Satisfactory growth of the cells was confirmed.

Example 4

Mass Continuous Culturing of Conditioned CHO-K1 Cells Using Porous Polyimide Films Ten 4 cm×10 cm-square porous polyimide films were subjected to dry heat sterilization at 180° C. for 30 minutes, and placed on a sterilizing plate with the A-surface of the mesh structure facing upward. Separately, 5 ml of a CHO-K1 cell suspension was prepared with the 0.5% FBS-conditioned CHO-K1 cells suspended at $2.4 \times 10^6$ cells per milliliter of medium (of which $2.3 \times 10^6$ were viable cells and $9.0 \times 10^4$ were dead cells, for a viable cell rate of 96%). A 0.5 ml portion of the cell suspension was added to each of the 10 sterilized porous polyimide films, and leveled with a cell scraper. After standing for several minutes, the sheets were slightly moved to cause the suspension to pass through, after which the 10 cell-seeded sheets were layered on a metal mesh of the same shape as the sheets. A nonwoven fabric was then placed over the layered sheets and set inside the culturing apparatus, the culture medium supply line was installed at the top, and then the entire culturing apparatus was transferred to a forced aerated $CO_2$ incubator by Tietech Co., Ltd. set to 37° C., thus completing preparation for culturing.

A 150 ml portion of 0.5% FBS-containing Ham medium was circulated at a pace of 1 ml/min, and continuous culturing was initiated. After 3 days, the medium was removed and replaced with 100 ml of fresh medium, and culturing was continued for another 9 days while continuing medium exchange at the same pace.

Figure 6:
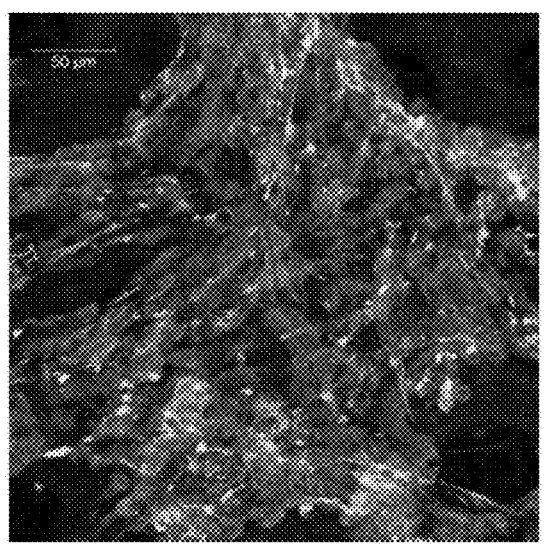
FIG. 6 shows results for mass culturing of CHO-K1 cells using a porous polyimide film.

Circulation of the medium was halted on the 12th day from the start of culturing, and the porous polyimide films and nonwoven fabric were removed. The cell count of the removed porous polyimide films, as the aggregate, was determined with CCK8, and a total count of $2.6 \times 10^8$ cells was confirmed. The estimated cell culturing density was $1.7 \times 10^8$/ml. The cell-grown porous polyimide films were partially cut out and fixed with formalin, staining was performed of the nuclei (DAPI), cell membranes (cell mask) and actin (phalloidin), and then a fluorescent microscope photograph was taken as shown in FIG. 6. Satisfactory cell growth was confirmed even when using conditioned cells.

Example 5

Mass Gas Phase-Exposed Culturing, Mass Subculturing, Long-Term Culturing

Following Example 4, ten 4 cm×10 cm-square porous polyimide films, with CHO-K1 cells adhering, were used as standard sheets, and ten sterilized porous polyimide films of the same size were layered on the top surfaces of the standard sheets with all of the A-surfaces of the mesh structures facing upward. Similarly, ten porous polyimide films were layered on the bottom surface of the standard sheets with all of the A-surfaces of the mesh structure facing upward. A nonwoven fabric was then placed over the 30 layered sheets and set inside the culturing apparatus used in Example 4 (FIG. 2), the culture medium supply line was installed at the top, and then the entire culturing apparatus was transferred to a forced aerated $CO_2$ incubator by Tietech Co., Ltd. set to 37° C., thus completing preparation for culturing.

Figure 7:
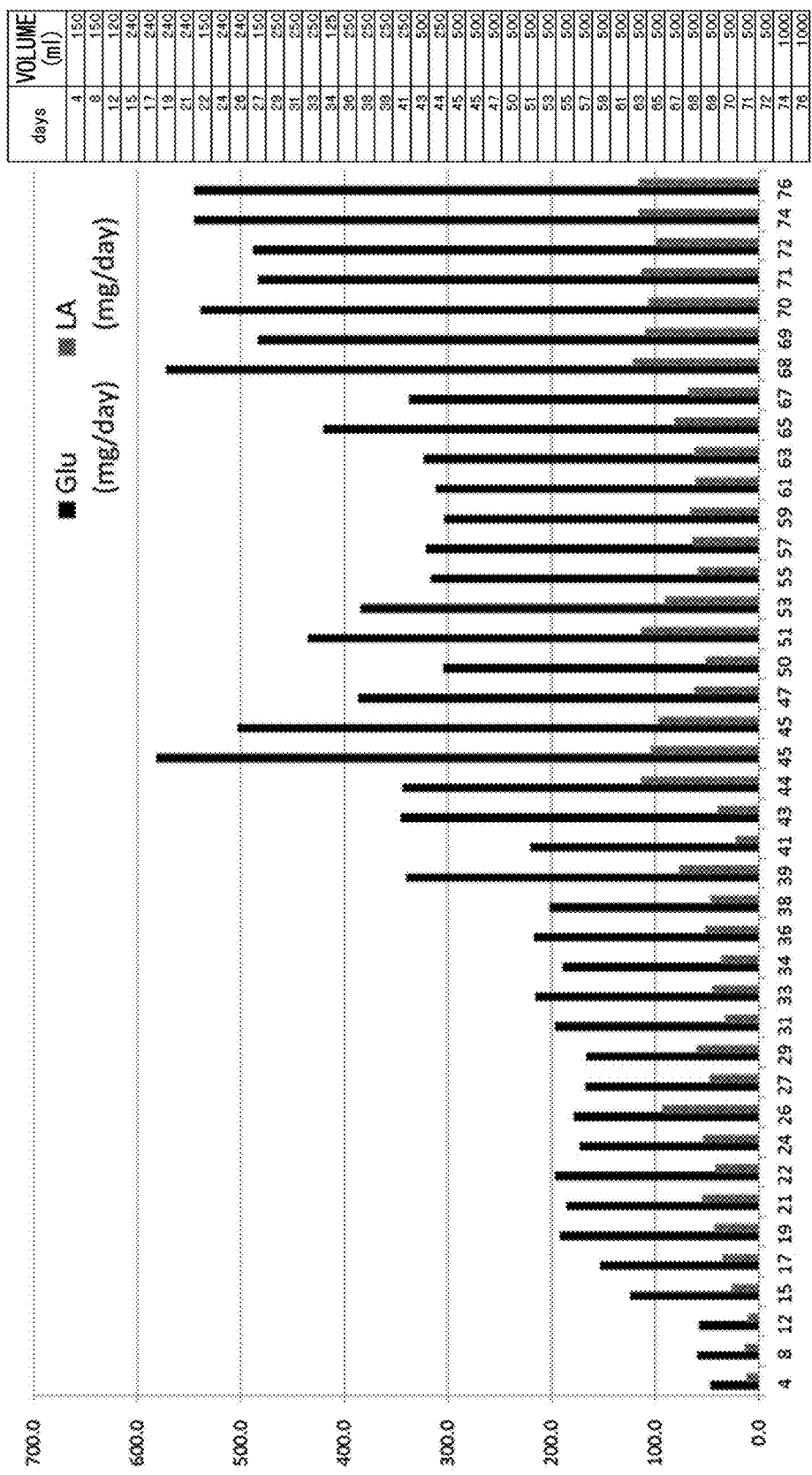
FIG. 7 is a graph showing culturing results for CHO-K1 cells using the cell culturing apparatus of the invention.

Next, 0.5% FBS-containing Ham medium was circulated at a pace of 2 ml/min, and continuous culturing was initiated. Culturing was continued for another 76 days or longer while continuing to exchange the medium at the pace shown in FIG. 7. The glucose consumption and lactic acid production during this time were measured by LC/MS (Shimadzu LCMS-2020). The results are shown in FIG. 7.

Example 6

For this example, the efficiency of the cell culture system using porous polyimide films was examined by comparison of the grown cell counts with cell culturing using G-CSF-producing CHO-K1 cells.

After setting 40 sterilized 1.4 cm-square porous polyimide films in a 2 cm×2 cm sterilized square vessel with the A-surfaces of the mesh structure facing upward, 100 μl of a suspension of $3.9 \times 10^5$ G-CSF-producing CHO-K1 cells per milliliter of medium (of which $3.5 \times 10^5$ were viable cells and $3.7 \times 10^4$ were dead cells, for a viable cell rate of 91%) was placed over them, and the liquid portion was allowed to pass through, to complete seeding. After suctioning off and discarding the passed liquid portion, 1 ml of Ham's-F12 medium containing 10% (20 sheets) or 1% (20 sheets) FBS was added as cell culture medium, and after transfer to a $CO_2$ incubator, culturing was continued. Medium exchange was performed twice a week, and after culturing for 14 days, the cell count was measured using CCK8, and the cultured cell count was found to be $3.9 \times 10^6$ per $cm^2$ in the 10% FBS-added Ham medium and $2.9 \times 10^6$ per $cm^2$ in the 1% FBS-added Ham medium, as the average for the 20 sheets under each of the culturing conditions.

Example 7

Figure 8:
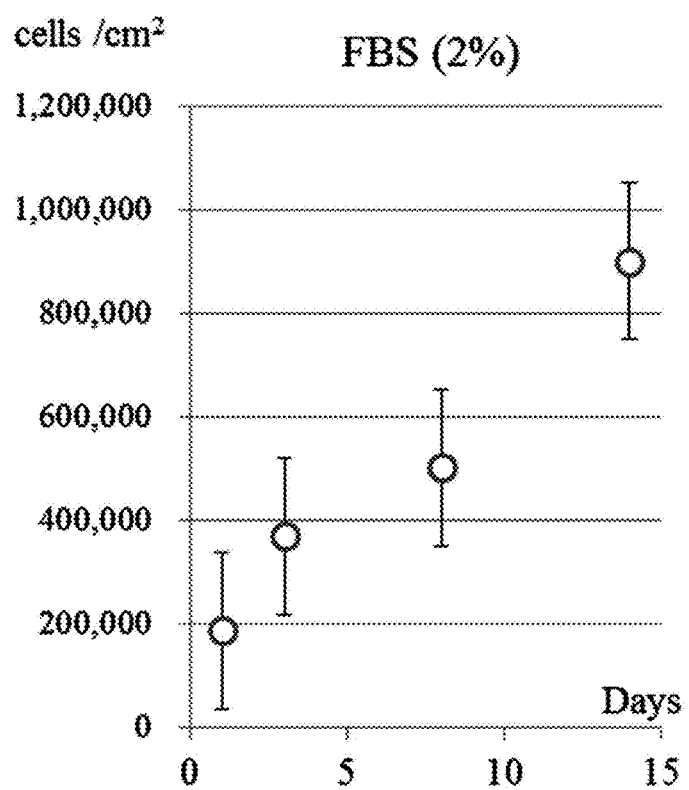
FIG. 8 is a graph showing culturing results for human anti-IL-8 antibody-producing CHO DP-12 cells.
Figure 9:
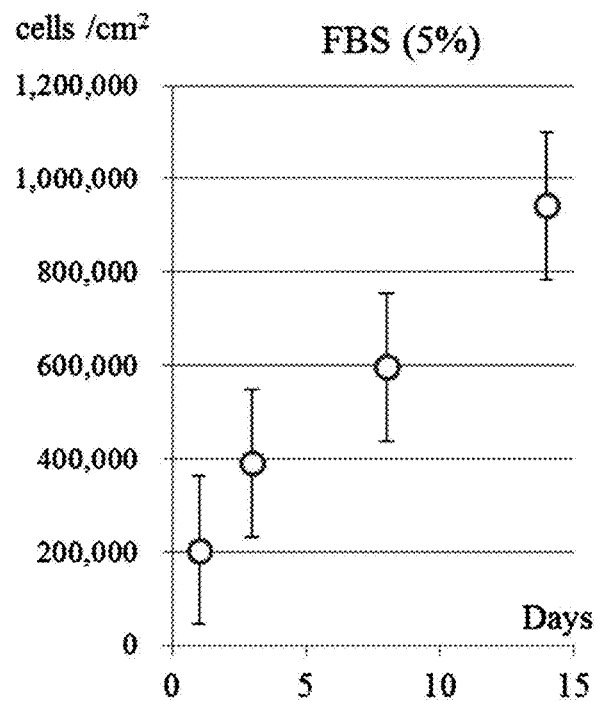
FIG. 9 is a graph showing culturing results for human anti-IL-8 antibody-producing CHO DP-12 cells.

After adding 0.5 ml of cell culture medium (2% FBS, IMDM, product of Wako Pure Chemical Industries, Ltd., or 5% FBS, IMDM, product of Wako Pure Chemical Industries, Ltd.) to a 2 cm×2 cm sterilized square vessel, the sterilized 1.4 cm-square porous polyimide films were each immersed with the A-surfaces of the mesh structure facing upward. A human anti-IL-8-producing CHO DP-12 cell suspension was added to the sheets in each medium at $4 \times 10^4$ cells per sheet, and continuous cell culturing was carried out, with medium exchange twice a week, while periodically measuring the cell count using CCK8. The experiment was conducted with 10 sheets under conditions of both 2% (FIG. 8) and 5% (FIG. 9) FBS, and satisfactory cell growth was observed.

Comparative Example 1

Mass Culturing of Gene Recombinant CHO-K1 Cells Using Commercially Available Three-Dimensional Culturing Scaffold Human G-CSF gene-transferred CHO-K1 cells were used for seeding into a commercially available three-dimensional culturing scaffold, and then mass culturing was carried out in a dish.

(1) Culturing with Alvetex®

1 ml of CHO-K1 cell medium (10% FBS-containing Ham's-F12 medium) was added to an insert cell of Alvetex® (cat. AVP004 by ReproCell) with a diameter of approximately 2.2 cm (seeding area: ~3.8 $cm^2$), and $5.0 \times 10^4$ human G-CSF gene recombinant CHO-K1 cells were seeded so as to be $2.0 \times 10^4/cm^2$ per unit area of the scaffold sheet.

The seeded vessel was incubated at 37° C. with 5% $CO_2$, and every 3 days the medium supernatant was collected and cell culture medium freshly added in the same manner as for seeding, while continuing the culturing. After 3 days, 6 days and 14 days, CCK8 was used to measure the cell count.

(2) Culturing with Biotex

After adding 1 ml of CHO-K1 cell medium (10% FBS-containing Ham's-F12 medium) to a cell of 3D Insert-PCL/-PS (3D Biotek, LLC, cat. PS152012-6) with a diameter of approximately 2.1 cm (seeding area: ~3.5 $cm^2$) and 4 ml into the outer vessel, $7.0 \times 10^4$ human G-CSF gene recombinant CHO-K1 cells were seeded so as to be $2.0 \times 10^4/cm^2$ per unit area of the scaffold sheet.

The seeded vessel was incubated at 37° C. with 5% $CO_2$, and every 3 days the medium supernatant was collected and cell culture medium freshly added in the same manner as for seeding, while continuing the culturing. After 3 days, 6 days and 14 days, CCK8 was used to measure the cell count.

(3) Culturing with Porous Polyimide Films

After adding 0.5 ml of CHO-K1 cell medium (10% FBS-containing Ham's-F12 medium) to a 2 cm×2 cm sterilized square vessel, ten sterilized 1.4 cm-square porous polyimide films (seeding area: 2 $cm^2$) were immersed in the medium with the A-surfaces facing upward. Human G-CSF gene recombinant CHO-K1 cells ($4.0 \times 10^4$) were seeded, at $2.0 \times 10^4/cm^2$ per unit area of the sheets.

The seeded vessel was incubated at 37° C. with 5% $CO_2$, and every 3 days the medium supernatant was collected and cell culture medium freshly added in the same manner as for seeding, while continuing the culturing. After 6 days and 14 days, CCK8 was used to measure the cell count.

<Comparative Verification>

Since each of the components had different areas and thicknesses and their cell culturing efficiencies were difficult to compare directly, it was necessary to compare the volume efficiencies after adjusting their areas and thicknesses. FIG. 10, therefore, shows the cell counts of cells cultured in the volume of each component expressed in terms of an area of 1 cm² and a thickness of 25 μm.

Comparative Example 2

Growth Comparison of Human Skin Fibroblasts
(1) Culturing with Alvetex®
1 ml of cell culture medium (2% FBS, Fibroblast Media, product of Lonza) was added to an insert cell of Alvetex® (cat. AVP004 by ReproCell) with a diameter of approximately 2.2 cm (seeding area: ~3.8 cm²), and a human skin fibroblast ($5.0 \times 10^4$) suspension was seeded.

The seeded vessel was incubated at 37° C. with 5% $CO_2$, and every 3 days the medium supernatant was collected and cell culture medium freshly added in the same manner as for seeding, while continuing the culturing. After 3 days, 6 days and 14 days, CCK8 was used to measure the cell count.
(2) Culturing with Biotex
After adding 1 ml of cell culture medium (2% FBS, Fibroblast Media product of Lonza) to a cell of 3D Insert-PCL/-PS (3D Biotek, LLC, cat. PS152012-6) with a diameter of approximately 2.1 cm (seeding area: ~3.5 cm²) and 4 ml into the outer vessel, a human skin fibroblast ($7.0 \times 10^4$) suspension was seeded so as to be $2.0 \times 10^4$/cm² per unit area of the scaffold sheet.

The seeded vessel was incubated at 37° C. with 5% $CO_2$, and every 3 days the medium supernatant was collected and cell culture medium freshly added in the same manner as for seeding, while continuing the culturing. After 3 days, 6 days and 14 days, CCK8 was used to measure the cell count.
(3) Culturing with Porous Polyimide Film
After adding 1 ml of cell culture medium to a 2 cm×2 cm sterilized square vessel, a sterilized 1.4 cm-square porous polyimide film (seeding area: 2 cm²) was immersed in the medium with the A-surface facing upward. Human skin fibroblasts were seeded at $2 \times 10^4$/cm² per unit area of the sheet.

Figure 11:
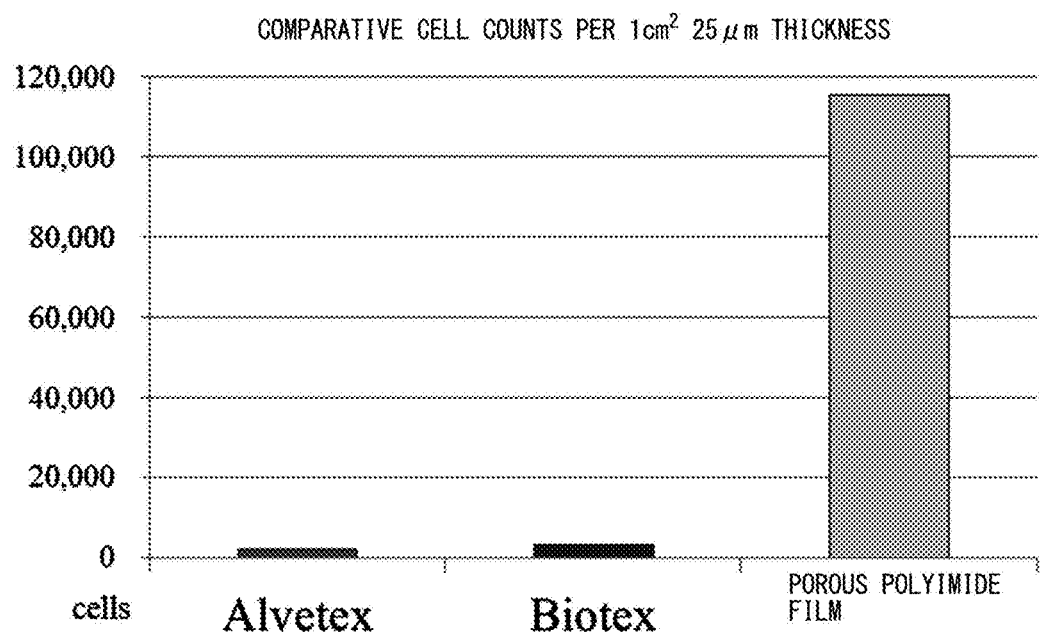
FIG. 11 is a graph showing culturing results for human fibroblasts using porous polyimide films and a commercially available three-dimensional culture scaffold.

The seeded vessel was incubated at 37° C. with 5% $CO_2$, and every 3 days the medium supernatant was collected and cell culture medium freshly added in the same manner as for seeding, while continuing the culturing. After 18 days, CCK8 was used to measure the cell count.
<Comparative Verification>
Since each of the components had different areas and thicknesses and their cell culturing efficiencies were difficult to compare directly, it was necessary to compare the volume efficiencies after adjusting their areas and thicknesses. FIG. 11, therefore, shows the cell counts of cells cultured in the volume of each component expressed in terms of an area of 1 cm² and a thickness of 25 μm.

What is claimed is:

1. A mass cell culturing method including:
    (1) applying cells to a porous polyimide film, and
    (2) applying the porous polyimide film to which the cells have been applied, to a cell culture medium and performing culturing the porous polyimide film to which the cells have been applied, until the number of cells reaches $1.0 \times 10^6$ or more per milliliter of medium, or until the number of cells per square centimeter of the porous polyimide film reaches $1.0 \times 10^5$,
    wherein the porous polyimide film has a multilayer structure having at least two surface layers (an A-surface and a B-surface), and a macro-void layer sandwiched between the two surface layers,
    a mean pore size of the holes in the A-surface is smaller than a mean pore size of the holes in the B-surface, and the macro-void layer has a partition bonded to the surface layers (the A-surface and the B-surface), and a plurality of macro-voids surrounded by the partition and the surface layers (the A-surface and the B-surface).

2. The method according to claim 1, wherein two or more porous polyimide films layered either above and below or left and right are used in the cell culture medium.

3. The method according to claim 1, wherein the porous polyimide films are:
    i) folded,
    ii) wound into a roll,
    iii) connected as sheets or fragments by a filamentous structure, or
    iv) bound into a rope,
to be suspended or fixed in the cell culture medium in the cell culturing vessel.

4. The method according to claim 1, wherein in the culturing of step (2), all or some of the porous polyimide films are not in contact with the liquid phase of the cell culture medium.

5. The method according to claim 1, wherein in the culturing of step (2), the total volume of the cell culture medium in the cell culturing vessel is 10,000 times or less of the total sum of the porous polyimide film volume including the cell survival zone.

6. The method according to claim 1, wherein in the culturing of step (2), the total volume of the cell culture medium in the cell culturing vessel is 100 times or less of the total sum of the porous polyimide film volume including the cell survival zone.

7. The method according to claim 1, wherein the culturing in step (2) is carried out in a system in which a cell culture medium is continuously or intermittently supplied to a cell culturing vessel from cell culture medium supply means installed outside of the cell culturing vessel.

8. The method according to claim 7, wherein the cell culture medium is circulated between the cell culture medium supply means and the cell culturing vessel.

9. The method according to claim 7, wherein the system is a cell culturing apparatus including a culturing unit which is the cell culturing vessel, and a culture medium-supply unit which is the cell culture medium supply means, wherein
    the culturing unit is a culturing unit that houses one or more porous polyimide films to support cells, and that comprises a culture medium supply port and a culture medium discharge port, and
    the culture medium-supply unit is a culture medium-supply unit comprising a culture medium housing vessel, a culture medium supply line, and a liquid conveyance pump that conveys the medium continuously or intermittently through the culture medium supply line, the first end of the culture medium supply line contacting the medium in the culture medium housing vessel, and the second end of the culture medium supply line being in communication with the culturing unit interior via the culture medium supply port of the culturing unit.

10. The method according to claim 9, wherein the culturing unit is a culturing unit that does not comprise an air supply port and air discharge port.

11. The method according to claim 9, wherein the culturing unit further comprises a culture medium discharge line, the first end of the culture medium discharge line being connected to the culture medium housing vessel, the second end of the culture medium discharge line being in communication with the culturing unit interior via the culture medium discharge port of the culturing unit, and the medium being able to circulate through the culture medium-supply unit and the culturing unit.

12. The method according to claim 1, wherein the cells are selected from the group consisting of animal cells, insect cells, plant cells, yeast cells and bacteria.

13. The method according to claim 12, wherein the animal cells are cells derived from an animal belonging to the subphylum Vertebrata.

14. The method according to claim 12, wherein the bacteria are selected from the group consisting of lactic acid bacteria, *E. coli, Bacillus subtilis* and cyanobacteria.

15. The method according to claim 1, wherein the porous polyimide film is a porous polyimide film including a polyimide obtained from a tetracarboxylic dianhydride and a diamine.

16. The method according to claim 15, wherein the porous polyimide film is a colored porous polyimide film obtained by forming a polyamic acid solution composition including a polyamic acid solution obtained from a tetracarboxylic dianhydride and a diamine, and a coloring precursor, and then heat treating it at 250° C. or higher.

* * * * *